United States Patent
Wild et al.

(10) Patent No.: US 9,518,990 B2
(45) Date of Patent: Dec. 13, 2016

(54) SECERNIN-1 AS A MARKER FOR CANCER

(75) Inventors: Norbert Wild, Geretsried/Gelting (DE);
Marie-Luise Hagmann, Penzberg (DE); Johann Karl, Peissenberg (DE); Julia Riedlinger, Munich (DE); Markus Roessler, Germering (DE); Michael Tacke, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 830 days.

(21) Appl. No.: 13/272,399

(22) Filed: Oct. 13, 2011

(65) Prior Publication Data
US 2012/0028835 A1 Feb. 2, 2012

Related U.S. Application Data

(63) Continuation of application No. PCT/EP2010/003139, filed on May 21, 2010.

(30) Foreign Application Priority Data

May 29, 2009 (EP) ..................... 09161524

(51) Int. Cl.
G01N 1/00 (2006.01)
G01N 33/00 (2006.01)
G01N 33/48 (2006.01)
G01N 33/50 (2006.01)
G01N 33/53 (2006.01)
G01N 33/574 (2006.01)

(52) U.S. Cl.
CPC .............. *G01N 33/57484* (2013.01)

(58) Field of Classification Search
CPC .......... G01N 1/00; G01N 33/00; G01N 33/48; G01N 33/50; G01N 33/53; G01N 33/574; G01N 33/57407; G01N 33/57484
See application file for complete search history.

(56) References Cited

U.S. PATENT DOCUMENTS

2007/0077556 A1 4/2007 Nelson et al.
2010/0233693 A1* 9/2010 Kopf-Sill et al. ................. 435/6

FOREIGN PATENT DOCUMENTS

WO 2004/057336 A3 7/2004
WO 2008/116592 A1 10/2008
WO 2009/019317 A1 2/2009

OTHER PUBLICATIONS

Ashida et al. Molecular features of the transition from prostatic intrepithelial neoplasia (PIN) to prostate cancer: genome-wide gene-expression profiles of prostate cancers and PINs. Cancer Research 64: 5963-5972, Sep. 1, 2004.*
Geisler et al. Identification and validation of potential new biomarkers for prostate cancer diagnosis and prognosis using 2 D-DIGE and MS. 2014.*
KIAA0193 and (alive[prop])—Gene—NCBI printed Jul. 2015.*
Brinton et al. (1997) Am. J. Obstet. Gynecol. 176:572-9.*
International Search Report issued Jul. 30, 2010 in PCT Application No. PCT/EP2010/003139, 8 pages.
Aksoy, Saime et al., "Human Liver Nicotinamide N-Methyltransferase," The Journal of Biological Chemistry, May 20, 1994, pp. 14835-14840, vol. 269, No. 20.
Appella, E. and Anderson, C. W., "Signaling to p53: breaking the posttranslational modification code," Pathologie et Biologie, 2000, pp. 227-245, vol. 48.
Breiman, Leo, "Random Forests," Machine Learning, 2001, pp. 5-32, vol. 45.
Buccheri, Gianfranco and Ferrigno, Domenico, "Identifying Patients at Risk of Early Postoperative Recurrence of Lung Cancer: A New Use of the Old CEA Test," The Annals of Thoracic Surgery, 2003, pp. 973-980, vol. 75.
Duffy, M. J., "Clinical Uses of Tumor Markers: A Critical Review," Critical Reviews in Clinical Laboratory Sciences, 2001, pp. 225-262, vol. 38, No. 3.
Friedman, Jerome H., "Regularized Discriminant Analysis," Journal of the American Statistical Association, Mar. 1989, pp. 165-175, vol. 84, No. 405.
Fukasawa, Toshio et al., "Clinical Evaluation of Serum NSE and CEA in Primary Lung Cancer Patients," Japanese Journal of Cancer and Chemotherapy, May 1986, pp. 1862-1867, vol. 13, No. 5, Abstract in English.
Goldstein, Leslie A. et al., "Molecular cloning of seprase: a serine integral membrane protease from human melanoma," Biochimica et Biophysica Acta, 1997, pp. 11-19, vol. 1361.
Henry, Leonard R. et al., "Clinical Implications of Fibroblast Activation Protein in Patients with Colon Cancer," Clinical Cancer Research, Mar. 15, 2007, pp. 1736-1741, vol. 13, No. 6.
Hillier, LaDeana W. et al., "The DNA sequence of human chromosome 7," Nature, Jul. 10, 2003, pp. 157-164, vol. 424.
Kassem, Heba Sh. et al., "A Potential Role of Heat Shock Proteins and Nicotinamide N-Methyl Transferase in Predicting Response to Radiation in Bladder Cancer," International Journal of Cancer, 2002, pp. 454-460, vol. 101.
Lee, Kyung N. et al., "A novel plasma proteinase potentiates α2-antiplasmin inhibition of fibrin digestion," Blood, May 15, 2004, pp. 3783-3788, vol. 103, No. 10.
Lee, Kyung N. et al., "Antiplasmin-cleaving enzyme is a soluble form of fibroblast activation protein," Blood, Feb. 15, 2006, pp. 1397-1404, vol. 107, No. 4.
Merle, P. et al., "Early CYFRA 21-1 variation predicts tumor response to chemotherapy and survival in locally advanced non-small cell lung cancer patients," The International Journal of Biological Markers, pp. 310-315, vol. 19, No. 4.

(Continued)

*Primary Examiner* — Alana Harris Dent
(74) *Attorney, Agent, or Firm* — Stinson Leonard Street LLP

(57) ABSTRACT

Disclosed is a method aiding in the assessment of cancer. It involves the use of the secernin-1 protein (SCRN1) as a universal marker of different cancer types. More specifically disclosed is a method for assessing cancer from a liquid sample derived from an individual by measuring SCRN1 in the sample. Measurement of SCRN1 can, e.g., be used in the early detection of cancer or in the surveillance of patients who undergo surgery.

4 Claims, 14 Drawing Sheets

(56) References Cited

OTHER PUBLICATIONS

Molina, R. et al., "Tumor Markers (CEA, CA 125, CYFRA 21-1, SCC and NSE) in Patients with Non-Small Cell Lung Cancer as an Aid in Histological Diagnosis and Prognosis Comparison with the Main Clinical and Pathological Prognostic Factors,"Tumor Biology, 2003, pp. 209-218, vol. 24.

Nagase, Takahiro et al., "Prediction of the Coding Sequences of Unidentified Human Genes. V. The Coding Sequences of 40 New Genes (KIAA0161-KIAA0200) Deduced by Analysis of cDNA Clones from Human Cell Line KG-1," DNA Research, 1996, pp. 17-24, vol. 3.

Okamura, Atsushi et al., "Increased Hepatic Nicotinamide N-Methyltransferase Activity as a Marker of Cancer Cachexia in Mice Bearing Colon 26 Adenocarcinoma," Japanese Journal of Cancer Research, Jun. 1998, pp. 649-656, vol. 89.

Oliver, N. S. et al., "Glucose sensors: a review of current and emerging techology," Diabetic Medicine, 2009, pp. 197-210, vol. 26.

O'Neill, Eric E. et al., "Towards complete analysis of the platelet proteome," Proteomics, 2002, pp. 288-305, vol. 2.

Park, John E. et al., "Fibroblast Activation Protein, a Dual Specificity Serine Protease Expressed in Reactive Human Tumor Stromal Fibroblasts," The Journal of Biological Chemistry, Dec. 17, 1999, pp. 36505-36512, vol. 274, No. 51.

Petitjean, A. et al., "TP53 mutations in human cancers: functional selection and impact on cancer prognosis and outcomes, " Oncogene, 2007, pp. 2157-2165, vol. 26.

Pineiro-Sanchez, "Identification of the 170-kDa Melanoma Membrane-bound Gelatinase (Seprase) as a Serine Integral membrane Protease," The Journal of Biological Chemistry, Mar. 21, 1997, pp. 7595-7601, vol. 272, No. 12.

Ruczinski, Ingo et al., "Logic Regression," Journal of Computational and Graphical Statistics, 2003, pp. 475-511, vol. 12, No. 3.

Sabo, Edmond et al., "Expression Analysis of Barrett's Esophagus-Associated High-Grade Dysplasia in Laser Capture Microdissected Archival Tissue," Clinical Cancer Research, Oct. 15, 2008, pp. 6440-6448, vol. 14, No. 20.

Scanlan, Matthew J. et al., "Molecular cloning of fibroblast activation protein $\alpha$, a member of the serine protease family selectively expressed in stromal fibroblasts of epithelial cancers," Proceedings of the National Academy of Sciences, Jun. 1994, pp. 5657-5661, vol. 91.

Schneider, Joachim et al., "Fuzzy logic-based tumor-marker profiles improved sensitivity in the diagnosis of lung cancer," International Journal of Clinical Oncology, 2002, pp. 145-151, vol. 7.

Soussi, Thierry, "p53 Antibodies in the Sera of Patients with Various Types of Cancer: A Review," Cancer Research, Apr. 1, 2000, pp. 1777-1788, vol. 60.

Suda, Takako et al., "Identification of secernin 1 as a novel immunotherapy target for gastric cancer using the expression profiles of cDNA microarray," Cancer Science, May 2006, pp. 411-419, vol. 97, No. 5.

Tan, Eng M. and Zhang, Jianying, "Autoantibodies to tumor-associated antigens: reporters from the immune system," Immunological Reviews, 2008, pp. 328-340, vol. 222.

Wagner, Henry Jr., "Postoperative Adjuvant Therapy for Patients With Resected Non-Small Cell Lung Cancer: Still Controversial After all These Years," Chest, 2000, pp. 110S-118S, vol. 117.

Way, Gemma et al., "Purification and Identification of Secernin, a Novel Cytosolic Protein that Regulates Exocytosis in Mast Cells," Molecular Biology of the Cell, Sep. 2002, pp. 3344-3354, vol. 13.

Yamashita, Satoshi et al., "Chemical genomic screening for methylation-silenced genes in gastric cancer cell lines using 5-aza-2'-deoxycytidine treatment and oligonucleotide microarray," Cancer Science, Jan. 2006, pp. 64-71, vol. 97, No. 1.

Zhang, Jian-Ying et al., "Enhancement of Antibody Detection in Cancer Using Panel of Recombinant Tumor-associated Antigens," Cancer Epidemiology, Biomarkers & Prevention, Feb. 2003, pp. 136-143, vol. 12.

Zweig, Mark H. and Campbell, Gregory, "Receiver-Operating Characteristic (ROC) Plots: A Fundamental Evaluation Tool in Clinical Medicine," Clinical Chemistry, 1993, pp. 561-577, vol. 39, No. 4.

Olivier, M. et al., "Recent advances in p53 research: an interdisciplinary perspective," Cancer Gene Therapy, 2009, pp. 1-12, vol. 16.

* cited by examiner

Fig. 14

```
  1  MAAPPSYCP VAPPPRAKDG LVVFGKNGAR PRDEVQEVVY FGAADHEPES
 51  KVECTYISID QVPRTYAIMI SRPARLWGAR NGANERGVCI ANEAINTREP
101  AAKIEALLGM DLVRLGLERG ETAKEALDVI VSLLEERQQG GNYFEDANSC
151  HSFQSAYLIV DRDEANVLET IGKYWAAEKV TEGVRCICSQ LSLYTRMDAE
201  HFELPSYAQS QDNNTGESEF NFSEVFSFVE DHLDCGASKD SLEKQEESIT
251  VQIMMNTLRS KASGVCIDSE FFLTTASGVS VLPQNRSSPC IHYFTGIPDP
301  SRGIFKPFIP VDDVRLVPKT QSPCFGDDDP AKKEPRFQEK PDRRHELYKA
351  HENAPAIIES DQEQQRRLRS TMLELERQGL EAMEEILTSS EPLDPAEVGD
401  LFYSCVDTEI KFTK
```

SECERNIN-1 AS A MARKER FOR CANCER

RELATED APPLICATIONS

This application is a continuation of PCT/EP2010/003139 filed May 21, 2010 and claims priority to EP 09161524.5 filed May 29, 2009.

SEQUENCE LISTING

The instant application contains a Sequence Listing which has been submitted in ASCII format via EFS-Web and is hereby incorporated by reference in its entirety. Said ASCII copy, created on Oct. 12, 2011, is named 26148US.txt, and is 4,803 bytes in size.

FIELD

The present invention relates to a method aiding in the assessment of cancer. It discloses the use of the secernin-1 protein (SCRN1) as a universal marker of different cancer types. Furthermore, it especially relates to a method for assessing cancer from a liquid sample, derived from an individual by measuring SCRN1 in said sample. Measurement of SCRN1 can, e.g., be used in the early detection of cancer or in the surveillance of patients who undergo surgery.

BACKGROUND

Cancer remains a major public health challenge despite progress in detection and therapy. Cancer cells are characterized by the production of cancer-associated marker proteins. Cancer-associated proteins are found both in the tissues and in the bodily fluids of an individual who carries cancer cells. Their levels usually are low at the early stages of the carcinogenic progress and increase during the disease's progression and only in rare cases proteins are observed showing a decreased level in the course of disease progression. The sensitive detection of these proteins is an advantageous and promising approach for the diagnosis of cancer, in particular in an early stage diagnosis of cancer. The most prevalent cancer types are breast cancer (BC), lung cancer (LC) and colorectal cancer (CRC).

The most important therapeutic approaches for solid tumors are:
 a) surgical resection of the tumor,
 b) chemotherapy,
 c) radiation therapy,
 d) treatment with biologicals, like anti-tumor antibodies or anti-angiogenic antibodies and
 e) a combination of the above methods.

Surgical resection of the tumors is widely accepted as a first line treatment for early stage solid tumors. Most cancers, however, are detected only when they become symptomatic, i.e., when patients already are in a rather late stage of disease progression.

The staging of cancer is the classification of the disease in terms of extent, progression, and severity. It groups cancer patients so that generalizations can be made about prognosis and the choice of therapy.

The different stages of CRC used to be classified according to Dukes' stages A to D. Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), Sobin, L. H., Wittekind, Ch. (eds.), TNM Classification of Malignant Tumours, sixth edition (2002)). Once the TNM status is determined the patients are grouped into disease stages that are denoted by Roman numerals ranging form I to IV with IV being the most advanced disease stage. TNM staging and UICC disease stages correspond to each other as shown in the following table taken from Sobin and Wittekind (eds.), supra.

TABLE 1

| Interrelation of TNM staging and UICC disease stages | | | |
|---|---|---|---|
| UICC disease stage | T staging | N staging | M staging |
| Stage 0 | Tis | N0 | M0 |
| Stage I | T1, T2 | N0 | M0 |
| Stage IIA | T3 | N0 | M0 |
| Stage IIB | T4 | N0 | M0 |
| Stage IIIA | T1, T2 | N1 | M0 |
| Stage IIIB | T3, T4 | N1 | M0 |
| Stage IIIC | Any T | N2 | M0 |
| Stage IV | Any T | Any N | M1 |

What is especially important is that early diagnosis cancer, e.g., of CRC translates to a much better prognosis. In CRC malignant tumors of the colorectum arise from benign tumors, i.e., from adenoma. Therefore, best prognosis have those patients diagnosed at the adenoma stage. Patients diagnosed as early as in stage $T_{is}$, N0, M0 or T1-3; N0; M0, if treated properly have a more than 90% chance of survival 5 years after diagnosis as compared to a 5-years survival rate of only 10% for patients diagnosed when distant metastases are already present.

Current detection methods including imaging methods, such as X-ray or nuclear resonance imaging in theory might at least partially be appropriate for use as a general screening tool. However, they are very costly and not affordable to health care systems for a general and broad use in mass screenings of large numbers of subjects, particularly for subjects without any tumor symptoms.

Thus, it is an object of the present invention to provide a simple and cost-efficient procedure of tumor assessments, e.g., to identify individuals suspect of having cancer. For this purpose, a general tumor marker which is detectable in body fluids, e.g., blood or serum or plasma or a panel of such markers, would be desirable.

A number of serum tumor markers are already in clinical use. For example the soluble 30 kDa fragment of cytoceratin 19 (CYFRA 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor and Diagnose, T H Books Verlagsgesellschaft, Frankfurt/Main, Germany (2000)).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum or plasma are the most widely used sources of sample in clinical routine. The identification of an early tumor marker that would aid in the reliable cancer detection or provide early prognostic information could lead to a method that would greatly aid in the diagnosis and in the management of this disease. Therefore, an urgent clinical need exists to improve the in vitro assessment of cancer and in particular of LC. It is especially important to improve the early diagnosis of cancer, e.g., LC, since for patients diagnosed early on chances of survival are much higher as compared to those diagnosed at a progressed stage of disease.

The clinical utility of biochemical markers in lung cancer has recently been reviewed (Duffy, M. J., Crit. Rev. Clin. Lab. Sci. 38 (2001) 225-262).

CYFRA 21-1 is currently regarded to be the best of the presently known tumor markers for lung cancer. Even though not organ-specific it is predominantly found in lung tissue. Sensitivity of CYFRA 21-1 for lung cancer is described to be between 46-61% at a specificity of 95% towards other benign lung diseases. Increased serum levels of CYFRA 21-1 are also associated with pronounced benign liver diseases, renal insufficiency and invasive bladder cancer. CYFRA 21-1 testing is recommended for postoperative therapy surveillance.

CEA belongs to the group of carcinofetal antigens, usually produced during embryogenesis. CEA is not organ-specific and predominantly used for monitoring of colorectal cancer. Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. The primary use of CEA is in monitoring colon cancer, especially when the disease has metastasized. However, a variety of cancers can produce elevated levels of CEA, including breast cancer. A preferred use of CEA is therapy surveillance of lung cancer.

NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While sensitivity for SCLC at 95% specificity is reported to be 60-87%, performance of NSE testing for NSCLC is poor (7-25%). NSE is recommended for therapy surveillance of SCLC.

CA 19-9 (carbohydrate antigen 19-9), a sialylated Lewis (a) antigen) on a glycolipid is a tumor marker for gastrointestinal cancers. It occurs in fetal gastric, intestinal and pancreatic epithelia. Low concentrations can also be found in adult tissue in the liver, lungs, and pancreas. There is no correlation between tumor mass and the CA 19-9 assay values Therefore the determination of CA 19-9 cannot be used for the early detection of pancreatic carcinoma. As the mucin is excreted exclusively via the liver, even slight cholestasis can lead to clearly elevated CA 19-9 serum levels in some cases. The marker is mainly used as an aid in the monitoring of disease status in those patients having confirmed pancreatic cancer (sensitivity 70-87%). 3-7% of the population have the Lewis a-negative/b-negative blood group configuration and are unable to express the mucin with the reactive determinant CA 19-9. This must be taken into account when interpreting the findings.

CA 125 is found in a high percentage of non-mucinous ovarian tumors of epithelial origin and can be detected in serum. Ovarian carcinoma accounts for about 20% of gynecological tumors. Although the highest CA 125 values occur in patients suffering from ovarian carcinoma, clearly elevated values are also observed in malignancies of the endometrium, breast, gastrointestinal tract, and various other malignancies. Increased values are sometimes found in various benign gynecological diseases such as ovarian cysts, ovarian metaplasia, endometriosis, uterus myomatosus or cervicitis. Slight elevations of this marker may also occur in early pregnancy and in various benign diseases (e.g., acute and chronic pancreatitis, benign gastrointestinal diseases, renal insufficiency, autoimmune diseases and others). Markedly elevated levels have been found in benign liver diseases such as cirrhosis and hepatitis. Extreme elevations can occur in any kind of ascites due to malignant and benign diseases. Although CA 125 is a relatively unspecific marker, it is today the most important tumor marker for monitoring the therapy and progress of patients with serous ovarian carcinoma. A sensitivity of 69-79% is reported for 82-93% specificity.

PSA ("prostate related antigen") is commonly tested tumor marker used in blood testing. PSA appears to have a high tissue specificity; the glycoprotein is found in normal prostatic epithelium and secretions but not in other tissues. PSA is highly sensitive for the presence of prostatic cancer. The elevation correlated with stage and tumor volume. It is predictive of recurrence and response to treatment. Finally, the antigen has prognostic value in patients with very high values prior to surgery are likely to relapse.

NNMT (nicotinamide N-methyltransferase; Swiss-PROT: P40261) has an apparent molecular weight of 29.6 kDa and an isoelectric point of 5.56. NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa (Aksoy, S. et al., J. Biol. Chem. 269 (1994) 14835-14840). Little is known in the literature about a potential role of the enzyme in human cancer. In one paper, increased hepatic NNMT enzymatic activity was reported as a marker for cancer cachexia in mice (Okamura, A. et al., Jpn. J. Cancer Res. 89 (1998) 649-656). In a recent report, down-regulation of the NNMT gene in response to radiation in radiation sensitive cell lines was demonstrated (Kassem, H. S. et al., Int. J. Cancer 101 (2002) 454-460). It has recently been found (WO 2004/057336) that NNMT will be of interest in the assessment of CRC.

ProGRP is a tumor marker, useful in the detection and monitoring of SCLC. Increased serum levels are also found in patients with nonmalignant lung/pleural diseases, such as idiopathic pulmonary fibrosis or sarcoidosis. While sensitivity for proGRP in the field of SCLC (at 95% specificity) is reported to be 47-86%, the performance of proGRP testing in the field of NSCLC is poor because the sensitivity is reported as being below 10%).

SCC was originally identified in squamous cell CA of the cervix. The sensitivity of SCC for LC in general is low (18-27%). Therefore, SCC testing is regarded to be not suitable for screening. However, due to a higher sensitivity for squamous cell CA, a preferred use for SCC is therapy surveillance, even though CYFRA 21-1 generally performs better.

p53 (TP53, cellular tumor antigen p53, tumor suppressor p53 or phosphoprotein p53) is a transcription factor inducing cell growth arrest or apoptosis (Appella, E. et al., Pathol. Biol. 48 (2000) 227-245). p53 acts as a tumor suppressor in many tumor types and inactivating mutations in its gene are the most common genetic events promoting cancer development in humans (reviewed in Olivier, M. and Petitjean, A., Cancer Gene Ther. 16 (2009) 1-12; Petitjean, A. et al., Oncogene 26 (2007) 2157-2165). p53 mutation is observed in 40-50% of colorectal carcinomas, and is associated with carcinoma aggressiveness (Soussi, T., Cancer Res. 60 (2000) 1777-1788). Mutations in p53 gene lead not only to the disruption of the protein function, but also to the expression of tumor-associated antigens (TAA) and initiation of the autoimmune response and generation of specific anti-p53 autoantibodies in sera of cancer patients (Zhang, J. Y. et al., Cancer Epidemiology, Biomarkers & Prevention 12 (2003) 136-143; Soussi, T., Cancer Res. 60 (2000) 1777-1788). Detection of anti-p53 autoantibodies in human sera is an emerging tool for the diagnosis and management of cancer. Dependent of the cancer type, the frequency of anti-p53 autoantibodies in sera range from 17.8% (CRC) to 16.1% (LC) and 7.8% (Breast Cancer) (Tan, E. M. and Zhang, J., Immunological Reviews 222 (2008) 328-340; Zhang, J. Y. et al., Cancer Epidemiology, Biomarkers & Prevention 12 (2003) 136-143).

Seprase, also known as fibroblast activation protein (FAP), is as a 170 kDa glycoprotein having gelatinase and dipeptidyl peptidase activity consisting of two identical monomeric seprase units (Pineiro-Sanchez, M. L. et al., J. Biol. Chem. 272 (1997) 7595-7601; Park, J. E. et al., J. Biol. Chem. 274 (1999) 36505-36512). The monomer of the human membrane bound seprase protein comprises 760 amino acids. Human seprase is predicted to have its first 4 N-terminal residues within the fibroblast cytoplasm, followed by a 21-residue transmembrane domain and then a 734 residue extracellular C-terminal catalytic domain (Goldstein et al., Biochim Biophys Acta. 1361 (1997) 11-19; Scanlan, M. J. et al., Proc Natl Acad Sci USA 91 (1994) 5657-5661). A shorter form of human seprase protein is known to a person skilled in the art as soluble seprase or circulating antiplasmin-cleaving enzyme (APCE) (Lee, K. N. et al., Blood 103 (2004) 3783-3788; Lee, K. N. et al., Blood 107 (2006) 1397-1404), comprising the amino acid positions 26-760 from Swissprot database Accession number Q12884. The dimer of soluble seprase is a 160 kDa glycoprotein consisting of two identical monomeric soluble seprase protein units. Piñeiro-Sánchez et al. (supra) found that a increased expression of seprase correlates with the invasive phenotype of human melanoma and carcinoma cells. Henry, L. R. et al., Clin. Cancer Res. 13 (2007) 1736-1741 describe that human colon tumor patients having high levels of stromal seprase are more likely to have aggressive disease progression and potential development of metastases or recurrence.

Human dipeptidyl peptidase IV (DPPIV), which is also known as CD26, is a 110 kDa cell surface molecule. The amino acid sequence of human DPPIV protein comprises 766 amino acids. It contains intrinsic dipeptidyl peptidase IV activity which selectively removes N-terminal dipeptide from peptides with proline or alanine in the third amino acid position. It interacts with various extracellular molecules and is also involved in intracellular signal transduction cascades. The multifunctional activities of human DPPIV are dependent on cell type and intracellular or extracellular conditions that influence its role as a proteolytic enzyme, cell surface receptor, co-stimulatory interacting protein and signal transduction mediator. Human DPPIV has a short cytoplasmatic domain from amino acid position 1 to 6, a transmembrane region from amino acid position 7 to 28, and an extracellular domain from amino acid position 29 to 766 with intrinsic dipeptidyl peptidase IV (DPPIV) activity. Human soluble dipeptidyl peptidase IV (soluble DPPIV) comprises the amino acid positions 29 to 766 from Swissprot database Accession number P27487. The dimer of soluble DPPIV is a 170 kDa glycoprotein consisting of two identical monomeric soluble DPPIV units.

Soluble DPPIV/seprase complex (DPPIV/seprase) refers to the soluble complex formed of a soluble DPPIV homodimer (170 kDa) and a soluble seprase homodimer (160 kDa) with a molecular weight of 330 kDa. Under certain conditions this complex may form a double complex having a molecular weight of 660 kDa.

With respect to marker profiles and aiming at improved diagnosis of lung cancer, a method was published (Schneider, J. et al., Int. J. Clin. Oncol. 7 (2002) 145-151) using fuzzy logic based classification algorithms to combine serum levels of CYFRA 21-1, NSE and C-reactive protein (CRP) which is a general inflammation marker. The authors report a sensitivity of 92% at a specificity of 95%. However in this study, for example the sensitivity of CYFRA 21-1 as a single tumor marker is reported to be at 72% at a specificity of 95%, which is significantly higher than in many other reported studies. Duffy, M. J., in Crit. Rev. Clin. Lab. Sci. 38 (2001) 225-262, report a sensitivity of between 46% and 61%. This unusual high performance achieved by Schneider et al., raises some doubts and might be due to several facts. Firstly, the collective of control patients seems to be younger than the patients collective, i.e., the groups are not well age-matched, and the patient collective comprises many late stages. Secondly and even more critical, the performance of the algorithm is checked on the samples of the training set which were used for the determination of the fuzzy logic qualifiers. Hence, these qualifiers are strictly speaking "tailor-made" for this set and not applied to an independent validation set. Under normal circumstances, is has to be expected that the same algorithm applied to a larger, independent, and well balanced validation set will lead to a significantly reduced overall performance.

It was the object of the present invention to investigate whether a biochemical marker can be identified which may be used in assessing cancer disease. In particular, the inventors of the present invention investigated whether a biochemical marker could be identified for the assessment of different cancer types, such as lung, breast, colon, prostate and kidney cancer in body fluids. In a very preferred aspect of the present invention, the identification of a biochemical marker for the assessment of lung cancer (LC) was investigated.

Surprisingly, it has been found that use of secernin-1 protein (SCRN1) can at least partially overcome some of the problems of the markers presently known in the state of the art.

Surprisingly, it has been found that a increased concentration of SCRN1 in the test sample is associated with the occurrence of cancer. It could be shown that SCRN1 is a marker which is not specific for a single type of cancer, but a marker for different types of cancer, i.e., a general tumor marker. Since SCRN1 appears to be rather specific for tumorigenic processes, the novel tumor marker SCRN1 has great potential to be of clinical utility with various classes of tumor types.

Surprisingly, it was found in the present invention that a determination of the concentration of SCRN1 in a sample and/or body fluid, allows the assessment of cancer, e.g., of lung, ovary, endometrium, melanoma, breast, head and neck, bladder, pancreas, colon, cervix, kidney or prostate cancer. Even more surprisingly, it was found that a increased concentration of SCRN1 or fragments thereof in a sample and/or body fluid compared to normal controls is indicative for the risk or occurrence of cancer.

The present invention relates to a method for assessing cancer in vitro comprising measuring in a sample the concentration of SCRN1 by an immunological detection method and using the measurement result, particularly the concentration determined, in the assessment of cancer.

SUMMARY OF THE INVENTION

In one embodiment the present invention relates to a method for assessing cancer in vitro comprising measuring in a liquid sample the concentration of a) secernin-1 protein (SCRN1) and/or fragments thereof, b) optionally one or more other marker of cancer, and c) using the measurement result of step (a) and optionally of step (b) in the assessment of cancer, wherein a increased concentration of SCRN1 is indicative for cancer.

Further the present invention relates to the use of SCRN1 in the assessment of cancer.

Further the present invention relates to the use of a combination of antibodies directed against SCRN1 in the assessment of cancer, wherein a increased concentration of SCRN1 is indicative for cancer.

Further the present invention discloses the use of a marker panel comprising SCRN1 and optionally one or more other marker for cancer in the assessment of cancer, wherein a increased concentration of SCRN1 is indicative for cancer.

Further the present invention relates to a kit for performing the method for assessing cancer in vitro comprising measuring in a sample the concentration of (a) SCRN1 and/or fragments thereof, (b) optionally one or more other marker of cancer, and (c) using the measurement result of step (a) and optionally of step (b) in the assessment of cancer, wherein a increased concentration of SCRN1 is indicative for cancer, comprising the reagents required to specifically measure SCRN1, and optionally the reagents required to specifically measure one or more other marker of cancer.

Surprisingly, it was found that a increased concentration of SCRN1 and/or fragments thereof in the test sample is associated with the occurrence of cancer. It could be shown that SCRN1 is a marker which is not specific for a single type of cancer, but a marker for different types of cancer, i.e., a general tumor marker. Since SCRN1 appears to be rather specific for tumorigenic processes, the novel tumor marker SCRN1 has great potential to be of clinical utility with various classes of tumor types.

BRIEF DESCRIPTION OF THE FIGURES

FIG. 14 shows the amino acid sequence of human SCRN1 protein; SwissProt database accession number: Q12765 (SEQ ID NO: 1).

DESCRIPTION OF THE SEQUENCES

Figure 1:
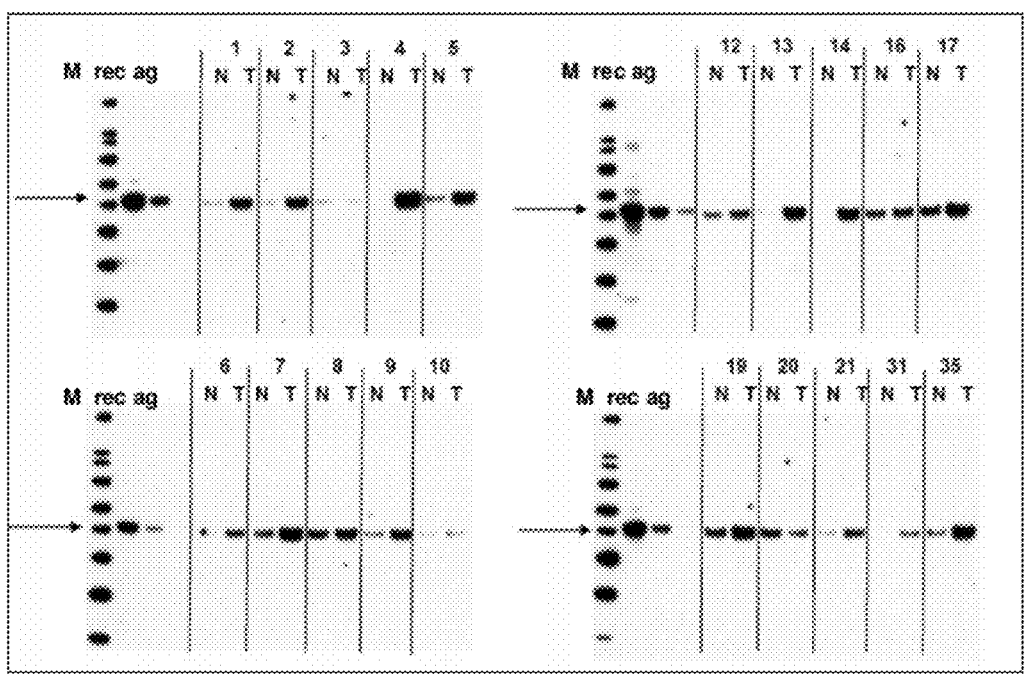
FIG. 1 shows a Western Blot analyses of 20 lung cancer tissue lysates. 15 µg total protein cancer (CA) tissue lysates and matched control tissue lysates were analyzed as described in example 3. M=molecular weight marker; T=tumor tissue lysate; N=matched control tissue lysate; rec ag=recombinantly produced secernin-1 (SCRN1); arrows indicate the position of secernin-1 (SCRN1).

SEQ ID NO: 1 shows the amino acid sequence of the human SCRN1 protein according to FIG. 14; SwissProt database accession number: Q12765.

SEQ ID NO: 2 shows the synthesized peptide extension.
SEQ ID NO: 3 shows the synthesized forward primer
SEQ ID NO: 4 shows the synthesized reverse primer

DETAILED DESCRIPTION OF THE INVENTION

In a preferred embodiment the present invention relates to a method for assessing cancer in vitro comprising measuring in a sample the concentration of SCRN1 and/or fragments thereof and using the measurement results, particularly the concentration determined in the assessment of cancer.

In another preferred embodiment the present invention relates to a method for assessing cancer in vitro comprising measuring in a liquid sample the concentration of (a) SCRN1 and/or fragments thereof, (b) optionally one or more other marker of cancer, and (c) using the measurement result of step (a) and optionally of step (b) in the assessment of cancer, wherein a increased concentration of SCRN1 is indicative for cancer.

The method of the present invention is suitable for the assessment of many different types of cancer. Increased concentrations of SCRN1 protein and/or fragments thereof in a sample as compared to normal controls have been found for example in specific cancer types like lung, ovary, endometrium, melanoma, breast, head and neck, bladder, pancreatic, colon, cervix, kidney or prostate cancer, respectively.

According to a preferred embodiment of the invention, the concentration of SCRN1 protein and/or fragments thereof is measured in a sample in order to assess cancer in vitro.

According to another preferred embodiment of the invention, the concentration of SCRN1 protein and/or fragments thereof is measured in a sample in order to assess specific cancer types, such as lung (LC), ovary (OC), endometrium (EC), melanoma (MM), breast (BC), head and neck (H/NC), bladder (BLC), pancreatic (PAC), colon (CRC), cervix (CC), kidney (KC) or prostate (PC) cancer in vitro.

According to another preferred embodiment of the invention, the concentration of SCRN1 protein and/or fragments thereof is measured in a sample in order to assess cancer, such as lung, colon, prostate, bladder, ovary, or breast cancer in vitro.

According to another preferred embodiment of the invention, the concentration of SCRN1 protein and/or fragments thereof is measured in a sample in order to assess cancer, such as lung cancer (LC) in vitro.

According to another preferred embodiment of the invention, the concentration of SCRN1 protein and/or fragments thereof is measured in a sample in order to assess cancer, such as ovary cancer (OC) in vitro.

According to another preferred embodiment of the invention, the concentration of SCRN1 protein and/or fragments thereof is measured in a sample in order to assess cancer, such as endometrium cancer (EC) in vitro.

According to another preferred embodiment of the invention, the concentration of SCRN1 protein and/or fragments thereof is measured in a sample in order to assess cancer, such as melanoma cancer (MM) in vitro.

According to another preferred embodiment of the invention, the concentration of SCRN1 protein and/or fragments thereof is measured in a sample in order to assess cancer, such as breast cancer (BC) in vitro.

According to another preferred embodiment of the invention, the concentration of SCRN1 protein and/or fragments thereof is measured in a sample in order to assess cancer, such as head and neck cancer (H/NC) in vitro.

According to another preferred embodiment of the invention, the concentration of SCRN1 protein and/or fragments thereof is measured in a sample in order to assess cancer, such as bladder cancer (BLC) in vitro.

According to another preferred embodiment of the invention, the concentration of SCRN1 protein and/or fragments thereof is measured in a sample in order to assess cancer, such as pancreatic cancer (PAC) in vitro.

According to another preferred embodiment of the invention, the concentration of SCRN1 protein and/or fragments thereof is measured in a sample in order to assess cancer, such as colorectal cancer (CRC) in vitro.

According to another preferred embodiment of the invention, the concentration of SCRN1 protein and/or fragments thereof is measured in a sample in order to assess cancer, such as cervix cancer (CC) in vitro.

According to another preferred embodiment of the invention, the concentration of SCRN1 protein and/or fragments thereof is measured in a sample in order to assess cancer, such as kidney cancer (KC) in vitro.

According to another preferred embodiment of the invention, the concentration of SCRN1 protein and/or fragments thereof is measured in a sample in order to assess cancer, such as prostate cancer (PC) in vitro.

One embodiment of the present invention refers to the mass screening of a population to distinguish between individuals which are probably free from cancer and individuals which might be classified as "suspect" cases. The latter group of individuals could then be subjected to further diagnostic procedures, e.g., by imaging methods or other suitable means.

A further embodiment of the present invention refers to an improvement of tumor marker panels which are suitable for the diagnosis of cancer in general or tumor marker panels which are suitable for the diagnosis of a specific tumor type, e.g., lung cancer.

The present invention is also directed to a method for assessing cancer in vitro by biochemical markers, comprising measuring in a sample the concentration of SCRN1 protein and/or fragments thereof and of one or more other markers specific for cancer, and using the measurement results, particularly the concentrations, determined in the assessment of cancer. Preferred markers for use in combination with SCRN1 are, on the one hand, markers which are general tumor markers (i.e., markers which are not specific for a single tumor type) or, on the other hand, specific tumor markers (markers which are specific for a single tumor type). Preferred markers, e.g., for the assessment of cancer, such as lung cancer or colon cancer, are CYFRA 21-1, CEA, NSE, CA 19-9, CA 125, PSA, proGRP, SCC, NNMT, anti-p53 autoantibodies, seprase and soluble DPPIV/seprase complex (DPPIV/seprase). These markers may be used individually each or in any combination together with SCRN1.

The present invention is also directed to a method for assessing cancer in vitro, such as lung cancer or colon cancer, by biochemical markers, comprising measuring in a sample the concentration of DPPIV/seprase and of one or more other cancer markers, e.g., one or more other markers of lung or colon cancer and using the measurement results, particularly concentrations determined in the assessment of cancer. It is preferred that the one or more other marker is selected from the group consisting of CYFRA 21-1, CEA, NSE, CA 19-9, CA 125, PSA, proGRP, SCC, NNMT, anti-p53 autoantibodies, seprase and DPPIV/seprase.

The present invention is also directed to the use of a marker panel comprising at least the marker SCRN1 and at least one other tumor marker(s), selected from the group consisting of CYFRA 21-1, CEA, NSE, CA 19-9, CA 125, PSA, proGRP, SCC, NNMT, anti-p53 autoantibodies, seprase and DPPIV/seprase, in the assessment of cancer, e.g., LC.

Preferably, the present invention is directed to a method for assessing cancer in vitro, such as lung cancer or colon cancer, by biochemical markers, comprising measuring in a sample the concentration of SCRN1 and/or fragments thereof and of one or more other cancer markers, e.g., one or more other markers of lung or colon cancer and using the measurement results, particularly concentrations determined in the assessment of cancer. It is preferred that the one or more other marker is selected from the group consisting of CYFRA 21-1, CEA, NSE, CA 19-9, CA 125, PSA, proGRP, SCC, NNMT, anti-p53 autoantibodies, seprase and DPPIV/seprase.

The present invention also relates to the use of SCRN1 protein and/or fragments thereof in the assessment of cancer, wherein a increased concentration of SCRN1 and/or fragments thereof is indicative for cancer.

The present invention also relates to the use of SCRN1 protein and/or fragments thereof in the assessment of cancer in vitro, wherein the sample is serum or plasma.

The present invention also relates to the use of SCRN1 in the assessment of several specific types of cancer, particularly lung, ovary, endometrium, melanoma, breast, head and neck, bladder, pancreas, colon, cervix, kidney or prostate cancer.

The present invention also relates to the use of SCRN1 in the assessment of several specific types of cancer, particularly lung, ovary, endometrium, melanoma, breast, head and neck, bladder, pancreas or colon cancer.

The present invention also relates to the use of SCRN1 in the assessment of several specific types of cancer, particularly lung, ovary, endometrium, melanoma, breast or head and neck cancer.

The present invention also relates to the use of an antibody directed against SCRN1 protein and/or fragments thereof in the assessment of cancer, wherein a increased concentration of SCRN1 and/or fragments thereof is indicative for cancer.

Preferably SCRN1 is detected in a sandwich-type immunoassay format (sandwich immunoassay).

The present invention also provides a kit for performing the method according to the present invention comprising at least the reagents required to specifically measure SCRN1 protein and/or fragments thereof and one or more other marker of cancer.

The present invention also provides a kit for performing the method according to the present invention comprising at least the reagents required to specifically measure SCRN1 protein and/or fragments thereof and optionally one or more markers of cancer, e.g., markers of lung, ovary, endometrium, melanoma, breast, head and neck, bladder, pancreas, colon, cervix, kidney or prostate cancer, as described above, wherein the other markers may be each used individually or in any combination thereof.

The present invention also provides a kit for performing the method according to the present invention comprising at least the reagents required to specifically measure SCRN1 and one or more other marker(s) selected from the group consisting of CYFRA 21-1, CEA, NSE, CA 19-9, CA 125, PSA, proGRP, SCC, NNMT, anti-p53 autoantibodies, seprase and DPPIV/seprase, and optionally auxiliary reagents for performing the measurement.

The present invention also provides a bio-chip array for performing the method according to the present invention to specifically measure SCRN1 and one or more other marker(s) selected from the group consisting of CYFRA 21-1, CEA, NSE, CA 19-9, CA 125, PSA, proGRP, SCC, NNMT, anti-p53 autoantibodies, seprase and DPPIV/seprase, and optionally auxiliary reagents for performing the measurement.

The present invention also provides a bio-chip array for performing the method according to the present invention to specifically measure SCRN1 and one or more other marker selected from the group consisting of CYFRA 21-1, CEA, NSE, CA 19-9, CA 125, PSA, proGRP, SCC, NNMT, anti-p53 autoantibodies, seprase and DPPIV/seprase in the assessment of cancer.

The present invention also provides a bio-chip array for performing the method according to the present invention to specifically measure SCRN1 and one or more other marker selected from the group consisting of CYFRA 21-1, CEA, NSE, CA 19-9, CA 125, PSA, proGRP, SCC, NNMT, anti-p53 autoantibodies, seprase and DPPIV/seprase, and optionally auxiliary reagents for performing the measurement in the assessment of cancer.

The term "measurement" preferably comprises a qualitative, semi-qualitative or a quantitative measurement of SCRN1 protein and/or fragments thereof in a sample. In a preferred embodiment the measurement is a semi-quantitative measurement, i.e., it is determined whether the concentration of SCRN1 is above or below a cut-off value. As the skilled artisan will appreciate, in a Yes-(presence) or No-(absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. A value above the cut-off value can for example be indicative for the presence of cancer. In particular a value above the cut-off value can for example be indicative for the presence of lung, colon, breast, ovary, cervix, head and neck, endometrium, melanoma, bladder, kidney, pancreatic, prostate, esophagus, stomach and/or bile duct cancer. In a further preferred embodiment the measurement of SCRN1 is a quantitative measurement. In further embodiments the concentration of SCRN1 is correlated to an underlying diagnostic question like, e.g., stage of disease, disease progression, or response to therapy.

In another preferred embodiment, the cut-off is set to result in a sensitivity of 90%, also preferred the cut-off is set to result in a sensitivity of 95%, or also preferred the cut-off is set to result in a sensitivity of 98%.

A value below the cut-off value can for example be indicative for the absence of cancer. In particular a value below the cut-off value can for example be indicative for the absence of lung, colon, breast, ovary, cervix, head and neck, endometrium, melanoma, bladder, kidney, pancreatic, prostate, esophagus, stomach and/or bile duct cancer.

In a further preferred embodiment the measurement of SCRN1 is a quantitative measurement. In further embodiments the concentration of SCRN1 is correlated to an underlying diagnostic question like, e.g., stage of disease, disease progression, or response to therapy.

Secernin-1 protein (SCRN1), Swiss-PROT ID: Q12765, is a cytosolic protein of 414 amino acids with a molecular weight of 46.4 kDa, characterized by the sequence given in SEQ ID NO: 1 (FIG. 14). The coding sequence of SCRN1 was predicted in 1996 by Nagase, T. et al. from the analysis of cDNA clones derived from bone marrow (Nagase, T. et al., DNA Res. 3 (1996) 17-24). More recently the respective gene was located on chromosome 7 and the gene structure was clarified (Hillier, L. N. et al., Nature 424 (2003) 157-164). While the gene is now well characterized, the biological role and function of SCRN1 is only partially understood. It regulates the secretion of mast cells and increases the sensitivity of the cells to stimulation with calcium (Way, G. et al., Mol. Biol. Cell 13 (2002) 3344-3354). SCRN1 was also detected in platelets by proteomics methods but without defining a function of the protein (O'Neill, E. E. et al., Proteomics 2 (2002) 288-305). In recent publications the level of RNA-expression has been linked to gastric cancer (Yamashita, S. et al., Cancer Sci. 97 (2006) 64-71), Suda, T. et al., Cancer Sci. 97 (2006) 411-419). A increased expression was also found in Barrett's esophagus, a premalignant condition, when cells where isolated by laser capture microdissection and the generated cDNA subsequently was analysed using Affymetrix microarrays (Sabo, E. et al., Clin. Cancer. Res. 14 (2008) 6440-6448). However, none of these studies presented a confirmation on protein level. So far the detection of the protein SCRN1 in body fluids as a diagnostic marker of cancer has not been described in the literature.

As used herein, each of the following terms has the meaning associated with it in this section.

The articles "a" and "an" are used herein to refer to one or to more than one (i.e., to at least one) of the grammatical object of the article. By way of example, "a marker" means one marker or more than one marker. The term "at least" is used to indicate that optionally one or more further objects may be present. By way of example, a marker panel comprising at least (the markers) SCRN1 and CYFRA 21-1 may optionally comprise one or more other marker.

The expression "one or more" denotes 1 to 50, preferably 1 to 20 also preferred 2, 3, 4, 5, 6, 7, 8, 9, 10, 12, or 15.

The terms "chip", "bio-chip", "polymer-chip" or "protein-chip" are used interchangeably and refer to a collection of a large number of probes, markers or biochemical markers arranged on a shared substrate which could be a portion of a silicon wafer, a nylon strip, a plastic strip, or a glass slide.

An "array," "macroarray" or "microarray" is an intentionally created collection of substances, such as molecules, markers, openings, microcoils, detectors and/or sensors, attached to or fabricated on a substrate or solid surface, such as glass, plastic, silicon chip or other material forming an array. The arrays can be used to measure the levels of large numbers, e.g., tens, thousands or millions, of reactions or combinations simultaneously. An array may also contain a small number of substances, e.g., one, a few or a dozen. The substances in the array can be identical or different from each other. The array can assume a variety of formats, e.g., libraries of soluble molecules, libraries of immobilized molecules, libraries of immobilized antibodies, libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

A "solid support" is insoluble, functionalized, polymeric material to which library members or reagents may be attached or covalently bound (often via a linker) to be immobilized or allowing them to be readily separated (by filtration, centrifugation, washing etc.) from excess reagents, soluble reaction by-products, or solvents.

The term "marker" or "biochemical marker" as used herein refers to a molecule to be used as a target for analyzing a patient's test sample. Examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (PI) or molecular weight (MW), or both e.g., as a result of alternative mRNA or pre-mRNA processing. The amino acid sequence of a variant is to 95% or more identical to the corresponding marker sequence. In addition, or in the alternative a marker polypeptide or a variant thereof may carry a post-translational modification. Non-limiting examples for posttranslational modifications are glycosylation, acylation, and/or phosphorylation.

SCRN1 proteins, particularly soluble forms of SCRN1 proteins and/or fragments thereof, are detected in appropriate samples. Preferred samples are tissue samples, tissue lysates or body fluids, such as blood, plasma, serum, urine, bronchioalveolar lavage (BAL; preferred in the case of suspected LC) or epithelial lining fluid (ELF; preferred in the case of suspected LC). Preferably, the sample is derived from a human subject, e.g., a tumor patient or a person in risk of a tumor or a person suspected of having a tumor. Also preferred SCRN1 is detected in a serum or plasma sample.

In a preferred embodiment according to the present invention, the concentration of SCRN1 protein and/or fragments thereof is determined. In one embodiment, the marker SCRN1 is specifically measured from a sample by use of a specific binding agent.

A specific binding agent is, e.g., a receptor for SCRN1, a lectin binding to SCRN1 or an antibody reactive with SCRN1. A specific binding agent has at least an affinity of $10^7$ l/mol for its corresponding target molecule. The specific binding agent preferably has an affinity of $10^8$ l/mol or also preferred of $10^9$ l/mol for its target molecule.

As the skilled artisan will appreciate the term specific is used to indicate that other biomolecules present in the sample do not significantly bind to the binding agent specific for SCRN1. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfil both the above minimum criteria for affinity as well as for specificity.

A specific binding agent preferably is an antibody reactive with SCRN1. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in rabbits may be used. However, clearly also polyclonal antibodies from different species, e.g., sheep or goat, as well as monoclonal antibodies can also be used. Since monoclonal antibodies can be produced in any amount required with constant properties, they represent ideal tools in development of an assay for clinical routine. The generation and the use of monoclonal antibodies to SCRN1 in a method according to the present invention, respectively, represent yet other preferred embodiments.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and theory of enzyme immunoassays, pp. 221-278, Burdon, R. H. and v. Knippenberg, P. H. (eds.), Elsevier, Amsterdam (1990), and various volumes of Methods in Enzymology, Colowick, S. P., and Caplan, N. O. (eds.), Academic Press), dealing with immunological detection methods, especially volumes 70, 73, 74, 84, 92 and 121.

As the skilled artisan will appreciate now that SCRN1 has been identified as a marker which is useful in the assessment of cancer, preferably lung cancer, various immunodiagnostic procedures may be used to reach a result comparable to the achievements of the present invention. For example, alternative strategies to generate antibodies may be used. Such strategies comprise amongst others the use of synthetic peptides, representing an epitope of SCRN1 for immunization. Alternatively, DNA immunization also known as DNA vaccination may be used.

For measurement the sample obtained from an individual is incubated with the specific binding agent for SCRN1 under conditions appropriate for formation of a binding agent SCRN1 complex. Such conditions need not be specified, since the skilled artisan without any inventive effort can easily identify such appropriate incubation conditions. The amount of binding agent SCRN1 complex is measured and used in the assessment of cancer, preferably of lung cancer. As the skilled artisan will appreciate there are numerous methods to measure the amount of the specific binding agent SCRN1 complex all described in detail in relevant textbooks (cf., e.g., Tijssen P., supra, or Diamandis, E. P. and Christopoulos, T. K. (eds.), Immunoassay, Academic Press, Boston (1996)).

Preferably SCRN1 is detected in a sandwich-type assay format (sandwich immunoassay). In such sandwich immunoassay, a first specific binding agent attached to a solid support is used to capture SCRN1 on the one side and a second specific binding agent, which is labeled to be directly or indirectly detectable, is used on the other side. The specific binding agents used in a sandwich-type assay format may be a combination of antibodies specifically directed against SCRN1.

A "marker of cancer" in the sense of the present invention is any marker that if combined with the marker SCRN1 adds relevant information in the assessment of cancer disease in the assessment of cancer in general or in the assessment of certain cancer types, e.g., in the assessment of LC, PRO, BLC, OC, BC or CRC. The information is considered relevant or of additive value if at a given specificity the sensitivity, or if at a given sensitivity the specificity, respectively, for the assessment of cancer can be improved by including said marker into a marker combination already comprising the marker SCRN1. In the preferred embodiment of cancer assessment, the improvement in sensitivity or specificity, respectively, is statistically significant at a level of significance of p=0.05, 0.02, 0.01 or lower. Preferably, the one or more other tumor marker is selected from the group consisting of CYFRA 21-1, CEA, NSE, CA 19-9, CA 125, PSA, proGRP, SCC, NNMT, anti-p53 autoantibodies, seprase and DPPIV/seprase.

The term "sample" as used herein refers to a biological sample obtained for the purpose of evaluation in vitro. In the methods of the present invention, the sample or patient sample preferably may comprise any body fluid. Preferred samples are tissue samples, tissue lysates or body fluids, such as whole blood, serum, plasma, urine, bronchioalveolar lavage (BAL; preferred in the case of suspected LC) or epithelial lining fluid ELF; preferred in the case of suspected LC), with serum or plasma being most preferred.

The term "tissue sample" and/or "tissue section" as used herein refers to a biological sample taken from a patient during surgery, therapeutic resections or a biopsy (e.g., incisional biopsy, excisional biopsy, core biopsy or needle aspiration biopsy) involving the removal of cells or tissues for the purpose of evaluation in vitro. When performing an analysis according to the present invention, the tissue sample material is used either directly or as a "tissue lysate". A "tissue sample" as used herein refers also to thin tissue slices usually accomplished through the use of a microtome. In any disclosed method embodiment involving a biological sample, such biological sample can be (but is not necessarily) mounted on a microscope slide, is a tissue section (such as a formalin-fixed and paraffin-embedded tissue section), and/or is a neoplastic tissue (such as, a lung cancer, colorectal cancer, head and neck cancer, gastric cancer, or glioblastoma).

A "tissue lysate", "cell lysate", "lysate", "lysed sample", "tissue extract" or "cell extract" as used herein refers to a sample and/or biological sample material comprising lysed tissue or cells, i.e., wherein the structural integrity of tissue or cells has been disrupted. To release the contents of cells or a tissue sample, the material is usually treated with enzymes and/or with chemicals to dissolve, degrade or disrupt the cellular walls and cellular membranes of such tissues or cells. The skilled artisan is fully familiar with appropriate methods for obtaining lysates. This process is encompassed by the term "lysis".

The term "assessing cancer" and in particular "assessing lung, ovary, endometrium, melanoma, breast, head and neck, bladder, pancreas, colon, cervix, kidney or prostate cancer" is used to indicate that the method according to the present invention will (alone or together with other markers or variables, e.g., the criteria set forth by the UICC (see above)) e.g., aid the physician to establish or confirm the absence or presence of cancer, in particular of LC or of CRC or aid the physician in the prognosis, the detection of recurrence (follow-up of patients after surgery) and/or the monitoring of treatment, especially of chemotherapy.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

Unless otherwise noted, technical terms are used according to conventional usage. Definitions of common terms in cell and molecular biology may be found in Lewin, B., Genes V, published by Oxford University Press (1994), ISBN 0-19-854287 9); Kendrew, J. et al. (eds.), The Encyclopedia of Molecular Biology, published by Blackwell Science Ltd. (1994), ISBN 0-632-02182-9); and Meyers, R. A. (ed.), Molecular Biology and Biotechnology: a Comprehensive Desk Reference, published by VCH Publishers, Inc. (1995), ISBN 1-56081-569 8).

In a preferred embodiment the present invention relates to a method for assessing cancer, e.g., LC, in vitro by biochemical markers, comprising measuring in a sample the concentration of SCRN1 and using the concentration determined in the assessment of cancer, e.g., LC.

In another preferred embodiment the present invention relates to a method for assessing LC in vitro by biochemical markers, comprising measuring in a sample the concentration of SCRN1 protein and/or fragments thereof and using the concentration determined in the assessment of LC.

The inventors of the present invention have surprisingly been able to detect a increased concentration of the marker SCRN1 in a significant percentage of samples derived from patients with cancer, in particular with lung, ovary, endometrium, melanoma, breast, head and neck, bladder, pancreas, colon, cervix, kidney or prostate cancer. Even more surprising they have been able to demonstrate that the increased concentration of SCRN1 in such sample obtained from an individual can be used in the assessment of cancer, in particular of the above-mentioned cancer diseases.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for many cancer types, e.g., for LC. As the skilled artisan will appreciate, no biochemical marker is diagnostic with 100% specificity and at the same time 100% sensitivity for a given multifactorial disease, for example for LC. Rather, biochemical markers, e.g., CYFRA 21-1, CEA, NSE, or as shown here SCRN1 can be used to assess with a certain likelihood or predictive value e.g., the presence, absence, or the severity of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then either interpreted independently, e.g., using an individual cut-off for each marker, or they are combined for interpretation.

In a further preferred embodiment the assessment of cancer according to the present invention is performed in a method comprising measuring in a sample the concentration of a) SCRN1 protein and/or fragments thereof, b) one or more other marker of cancer, and c) using the measurement result, e.g., the concentration determined in step (a) and step (b), respectively, in the assessment of cancer.

In the assessment of cancer the marker SCRN1 will be of advantage in one or more of the following aspects: screening; diagnostic aid; prognosis; monitoring of therapy such as chemotherapy, radiotherapy, and immunotherapy.

Screening

Screening is defined as the systematic application of a test to identify individuals, e.g., at risk individuals, for indicators of a disease, e.g., the presence of cancer. Preferably the screening population is composed of individuals known to be at higher than average risk of cancer. For example, a screening population for lung cancer is composed of individuals known to be at higher than average risk of lung cancer, like smokers, ex-smokers, and uranium-, quartz- or asbestos-exposed workers.

In the preferred embodiment, a tissue sample, tissue lysate or any body fluid such as whole blood, plasma, serum, urine, bronchioalveolar lavage (BAL; preferred in the case of suspected LC) or epithelial lining fluid (ELF; preferred in the case of suspected LC), is used as a sample in the screening for cancer, e.g., lung cancer.

For many diseases, no single biochemical marker in the circulation will ever meet the sensitivity and specificity criteria required for screening purposes. This appears to be also true for cancer and in particular for lung cancer. It has to be expected that a marker panel comprising a plurality of markers will have to be used in cancer screening. The data established in the present invention indicate that the marker SCRN1 will form an integral part of a marker panel appropriate for screening purposes. The present invention therefore relates to the use of SCRN1 as one marker of a cancer marker panel, i.e., a marker panel comprising SCRN1 and one or more additional marker for cancer screening purposes. In particular, the present invention relates to the use of SCRN1 as one marker of a general cancer marker panel. Such marker panel comprises the marker SCRN1 and one or more additional markers, e.g., general cancer markers and/or markers for the above-mentioned type of cancer.

A combination of markers significantly improves the value of the molecular assay. First, the sensitivity of the assay is significantly improved using the marker panel. Second, sophisticated statistical models permit ROC curve analysis of the multi marker assay, and the results confirm that the diagnostic accuracy is significantly increased compared to the best individual marker.

SCRN1 is also likely to contribute to marker panels for certain specific types of cancer, e.g., lung, ovary, endometrium, melanoma, breast, head and neck, bladder, pancreas, colon, cervix, kidney or prostate cancer.

Other preferred types of cancer to be assessed with a marker panel comprising SCRN1 are lung, ovary, endometrium, melanoma, breast, head and neck, bladder, pancreas or colon cancer.

Other preferred types of cancer to be assessed with a marker panel comprising SCRN1 are lung, ovary, endometrium, melanoma, breast or head and neck cancer.

Other preferred types of cancer to be assessed with a marker panel comprising SCRN1 are lung cancer (LC) or colon cancer (CRC).

A preferred type of cancer to be assessed with a marker panel comprising SCRN1 is lung cancer (LC).

The present data further indicate that certain combinations of markers will be advantageous in the screening for cancer.

For example, with reference to the preferred embodiment of screening cancer, the present invention also relates to the use of a marker panel comprising SCRN1 and at least one or more marker(s) selected from the group consisting of CYFRA 21-1, CEA, NSE, CA 19-9, CA 125, PSA, proGRP, SCC, NNMT, anti-p53 autoantibodies, seprase and DPPIV/seprase.

Diagnostic Aid

Markers may either aid the differential diagnosis of benign vs. malignant disease in a particular organ, help to distinguish between different histological types of a tumor, or to establish baseline marker values before surgery.

Today, important methods used in the detection of lung cancer are radiology and/or computed tomography (CT) scans. Small nodules, i.e., small regions of suspect tissue can be visualized by these methods. However, many of these nodules—more than 90% with CT—represent benign tissues changes, and only a minority of nodules represents cancerous tissue. Use of the marker SCRN1 may aid in the differentiation of benign versus malign disease.

In a preferred embodiment the marker SCRN1 is used in an immunohistological method in order to establish or confirm different histological types of cancer.

Since SCRN1 as a single marker might be superior to other markers, e.g., in the case of LC to other markers, like CEA or NSE, it has to be expected that SCRN1 will be used as a diagnostic aid, especially by establishing a baseline value before surgery. The present invention thus also relates to the use of SCRN1 for establishing a baseline value before surgery for cancer.

Prognosis

Prognostic indicators can be defined as clinical, pathological, or biochemical features of cancer patients and their tumors that predict with a certain likelihood the disease outcome. Their main use is to help to rationally plan patient management, i.e., to avoid undertreatment of aggressive disease and overtreatment of indolent disease, respectively. Molina, R. et al., Tumor Biol. 24 (2003) 209-218 evaluated the prognostic value of CEA, CA 125, CYFRA 21-1, SSC and NSE in NSCLC. In their study abnormal serum levels of the markers NSE, CEA, and LDH (lactate dehydrogenase) appeared to indicate shorter survival.

As SCRN1 alone significantly contributes to the differentiation of cancer patients, e.g., LC patients, from healthy controls, it has to be expected that it will aid in assessing the prognosis of patients suffering from cancer, preferably from LC. The level of preoperative SCRN1 will most likely be combined with one or more other marker for cancer and/or the TNM staging system. In a preferred embodiment SCRN1 is used in the prognosis of patients with LC.

Monitoring of Chemotherapy

Merle, P. et al., Int. J. of Biological Markers 19 (2004) 310-315 have evaluated CYFRA 21-1 serum level variations in patients with locally advanced NSCLC treated with induction chemotherapy. They conclude that early monitoring of CYFRA 21-1 serum levels may be a useful prognostic tool for tumor response and survival in stage III NSCLC patients. In addition, reports have described the use of CEA in monitoring the treatment of patients with LC (Fukasawa, T. et al., Cancer & Chemotherapy 13 (1986) 1862-1867) Most of these were retrospective, non-randomized and contained small numbers of patients. As in the case of the studies with CYFRA 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

It is expected that SCRN1 will be at least as good a marker for monitoring of chemotherapy as CYFRA 21-1 or CEA, respectively. The present invention therefore also relates to the use of SCRN1 in the monitoring of cancer patients and preferably of lung cancer (LC) patients under therapy.

In the monitoring of therapy in one preferred embodiment the measurements for SCRN1 and for at least one marker selected from the group consisting of CYFRA 21-1, CEA, NSE, CA 19-9, CA 125, PSA, proGRP, SCC, NNMT, anti-p53 autoantibodies, seprase and DPPIV/seprase will be combined and used in the assessment of lung cancer (LC).

Follow-Up

A large portion of LC patients who undergo surgical resection aimed at complete removal of cancerous tissue, later develop recurrent or metastatic disease (Wagner, H. Jr., Chest 117 (2000) S110-S118; Buccheri, G. et al., Ann. Thorac. Surg. 75 (2003) 973-980). Most of these relapses occur within the first 2-3 years after surgery. Since recurrent/metastatic disease is invariably fatal if detected too late, considerable research has focused on cancer relapse at an early and thus potentially treatable stage.

Consequently, many cancer patients, e.g., LC patients undergo a postoperative surveillance program which frequently includes regular monitoring with CEA. Serial monitoring with CEA one year after surgical resection has been shown to detect an early postoperative recurrent/metastatic disease with a sensitivity of approximately 29%, at a specificity of approximately 97%, even in the absence of suspicious symptoms or signs (Buccheri, G. et al., Ann. Thorac. Surg. 75 (2003) 973-980). Thus, the follow-up of patients with LC after surgery is one of the most important fields of use for an appropriate biochemical marker. Due to the high sensitivity of SCRN1 in the LC patients investigated it is likely that SCRN1 alone or in combination with one or more other marker will be of great help in the follow-up of LC patients, especially in LC patients after surgery. The use of a marker panel comprising SCRN1 and one or more other marker of LC in the follow-up of LC patients represents a further preferred embodiment of the present invention.

The present invention in a preferred embodiment relates to the use of SCRN1 in the diagnostic field of cancer. Preferably SCRN1 is used in the assessment of lung, ovary, endometrium, melanoma, breast, head and neck, bladder, pancreas, colon, cervix, kidney or prostate cancer, respectively.

In yet a further preferred embodiment the present invention relates to the use of SCRN1 as a marker molecule for cancer, e.g., for cancer in general or for specific types of cancer, such as lung, ovary, endometrium, melanoma, breast, head and neck, bladder, pancreas, colon, cervix, kidney or prostate cancer in combination with one or more further marker molecules for cancer. The further marker molecules may be cancer-type unspecific general marker molecules and/or cancer-type specific marker molecules, e.g., marker molecules for lung cancer. SCRN1 and the at least one further marker are used in the assessment of cancer, e.g., lung cancer in a liquid sample obtained from an individual. Preferred selected other cancer markers with which the measurement of SCRN1 may be combined are CYFRA 21-1, CEA, NSE, CA 19-9, CA 125, PSA, proGRP, SCC, NNMT, anti-p53 autoantibodies, seprase and DPPIV/seprase. In particular, preferred selected other LC markers with which the measurement of SCRN1 may be combined are CYFRA 21-1, CEA, CA 19-9, SCC, CA 125, proGRP and/or NSE. Yet further preferred the marker panel used in the assessment of cancer, e.g., LC comprises SCRN1 and at least one other marker molecule selected from the group consisting of CYFRA 21-1 and CEA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may, e.g., the case when diagnosing an infectious disease, like AIDS.

Frequently, however, the combination of markers is evaluated. Preferably the values measured for markers of a marker panel, e.g., for SCRN1 and CYFRA 21-1, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention, e.g., to the absence or presence of LC is selected from DA (i.e., Linear-, Quadratic-, Regularized Discriminant Analysis), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting Methods), or Generalized Linear Models (i.e., Logistic Regression). Details relating to these statistical methods are found in the following references: Ruczinski, I., et al, J. of Computational and Graphical Statistics 12 (2003) 475-511; Friedman, J. H., J. of the American Statistical Association 84 (1989) 165-175; Hastie, T. et al., The Elements of Statistical Learning, Springer Series in Statistics (2001); Breiman, L., et al., Classification and regression trees, California: Wadsworth (1984); Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O. et al., Pattern Classification, Wiley Interscience, 2nd edition (2001).

It is a preferred embodiment of the invention to use an optimized multivariate cut-off for the underlying combination of biological markers and to discriminate state A from state B, e.g., diseased from healthy. In this type of analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample.

Each point on the ROC plot represents a sensitivity/1−specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One preferred way to quantify the diagnostic accuracy of a laboratory test is to express its performance by a single number. Such an overall parameter, e.g., is the so-called "total error" or alternatively the "area under the curve=AUC". The most common global measure is the area under the ROC plot. By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Combining measurements of SCRN1 with other markers like CYFRA 21-1 or CEA, or with other markers of LC yet to be discovered, SCRN1 leads and will lead, respectively, to further improvements in assessment of LC.

In a preferred embodiment the present invention relates to a method for improving the diagnostic accuracy for cancer, e.g., LC versus healthy controls by measuring in a sample the concentration of at least SCRN1 and one or more other tumor markers selected from the group consisting of CYFRA 21-1, CEA, NSE, CA 19-9, CA 125, PSA, proGRP, SCC, NNMT, anti-p53 autoantibodies, seprase and DPPIV/seprase, respectively and correlating the concentrations determined to the presence or absence of cancer, e.g., LC, the improvement resulting in more patients being correctly classified as suffering from cancer, e.g., LC versus healthy controls as compared to a classification based on any single marker investigated alone.

In a further preferred embodiment the present invention relates to a method for improving the diagnostic accuracy for cancer, e.g., LC versus healthy controls by measuring in a sample the concentration of at least SCRN1 and CYFRA 21-1, and optionally of CEA and/or NSE, respectively and correlating the concentrations determined to the presence or absence of cancer, e.g., LC, the improvement resulting in more patients being correctly classified as suffering from cancer, e.g., LC versus healthy controls as compared to a classification based on any single marker investigated alone.

The following examples and the figure are provided to aid the understanding of the present invention, the true scope of which is set forth in the appended claims. It is understood that modifications can be made in the procedures set forth without departing from the spirit of the invention.

EXAMPLE 1

Identification of SCRN1 as a Potential Marker for Lung Cancer

Sources of Tissue

In order to identify tumor-specific proteins as potential diagnostic markers for lung cancer, analysis of two different kinds of tissue using proteomics methods is performed.

In total, tissue specimens from 20 patients suffering from lung cancer (LC) are analyzed. From each patient two different tissue types are collected from therapeutic resections: tumor tissue (>80% tumor) (T) and adjacent healthy tissue (N). The latter one serves as matched healthy control sample. Tissues are immediately snap frozen after resection and stored at −80° C. before processing. Tumors are diagnosed by histopathological criteria.

Tissue Preparation 0.8-1.2 g of frozen tissue are cut into small pieces, transferred to the chilled grinding jar of a mixer ball mill and completely frozen by liquid nitrogen. The tissue is pulverized in the ball mill, dissolved in the 10-fold volume (w/v) of lysis buffer (40 mM Na-citrate, 5 mM $MgCl_2$, 1% Genapol X-080, 0.02% Na-azide, Complete EDTA-free [Roche Diagnostics GmbH, Mannheim, Germany, Cat. No. 1 873 580]) and subsequently homogenized in a Wheaton glass homogenizer (20×loose fitting, 20×tight fitting). The homogenate is subjected to centrifugation (10' at 5,000×g), the supernatant is transferred to another vial and again subjected to centrifugation (15' at 20,000×g). The resulting supernatant contains the soluble proteins and is used for further analysis.

Isoelectric Focusing (IEF) and SDS-PAGE

For IEF, 3 ml of the suspension were mixed with 12 ml sample buffer (7 M urea, 2 M thiourea, 2% CHAPS, 0.4% IPG buffer pH 4-7, 0.5% DTT) and incubated for 1 h. The samples were concentrated in an Amicon Ultra-15 device (Millipore GmbH, Schwalbach, Germany) and the protein concentration was determined using the Bio-Rad protein assay (Cat. No. 500-0006; Bio-Rad Laboratories GmbH, München, Germany) following the instructions of the supplier's manual. To a volume corresponding to 1.5 mg of protein sample buffer was added to a final volume of 350 µl. This solution was used to rehydrate IPG strips pH 4-7 (Amersham Biosciences, Freiburg, Germany) overnight. The IEF was performed using the following gradient protocol: 1.) 1 minute to 500 V; 2.) 2 h to 3500 V; 3.) 22 h at constant 3500V giving rise to 82 kVh. After IEF, strips were stored at −80° C. or directly used for SDS-PAGE.

Prior to SDS-PAGE the strips were incubated in equilibration buffer (6 M urea, 50 mM Tris/HCl, pH 8.8, 30% glycerol, 2% SDS), for reduction DDT (15 min, +50 mg DTT/10 ml), and for alkylation IAA (15 min, +235 mg iodacetamide/10 ml) was added. The strips were put on 12.5% polyacrylamide gels and subjected to electrophoresis at 1 W/gel for 1 h and thereafter at 17 W/gel. Subsequently, the gels were fixed (50% methanol, 10% acetate) and stained overnight with Novex Colloidal Blue Staining Kit (Invitrogen, Karlsruhe, Germany, Cat No. LC6025, 45-7101).

Detection of SCRN1 as a Potential Marker for Lung Cancer

Each patient was analyzed separately by image analysis with the ProteomeWeaver software (Definiens AG, Germany, München). In addition, all spots of the gel were excised by a picking robot and the proteins present in the spots were identified by MALDI-TOF mass spectrometry (Ultraflex Tof/Tof, Bruker Daltonik GmbH, Bremen, Germany). For each patient, 3 gels from the tumor sample were compared with 3 gels each from adjacent normal tissue and analyzed for distinctive spots corresponding to differentially expressed proteins. SCRN1 was identified in tumor samples of 16 patients and only in 1 control sample. By this means, protein SCRN1 was found to be specifically expressed or strongly overexpressed in tumor tissue, respectively. It therefore qualified as a candidate marker for use in the diagnosis of lung cancer. The following tryptic peptides derived from SCRN1 were identified:

TABLE 2

Tryptic peptides identified by MALDI-TOF

| Peptide identified | Stretch of amino acids from SCRN1 (SEQ ID NO: 1) |
|---|---|
| DEVQEVVYFSAADHEPESK | 33-51 |
| VECTYISIDQVPR | 52-64 |
| EPAAEIEALLGMDLVR | 99-114 |
| DEAWVLETIGK | 163-173 |
| YWAAEKVTEGVR | 174-185 |
| DKASGVCIDSEFFLTTASGVSVLPQNR | 260-286 |
| ASGVCIDSEFFLTTASGVSVLPQNR | 262-286 |
| SSPCIHYFTGTPDPSR | 287-302 |
| SIFKPFIFVDDVK | 303-315 |
| FQEKPDR | 337-343 |
| AIIESDQEQGR | 356-366 |

EXAMPLE 2

Generation of Antibodies Against the Cancer Marker Protein SCRN1

Polyclonal antibody to the lung cancer marker protein SCRN1 is generated for further use of the antibody in the measurement of serum and plasma levels or concentrations in other body fluids of SCRN1 by immunodetection assays, e.g., Western Blotting and ELISA.

Recombinant Protein Expression in *E. coli*

In order to generate antibodies against SCRN1, the recombinant antigen is produced in *E. coli*: Therefore, the SCRN1-encoding region is PCR amplified from a full-length cDNA clone obtained from the German Resource Center for Genome Research (RZPD, Berlin, Germany) using the following primers:

```
Forward primer (SEQ ID NO. 3):
5'-acgtgaattcattaaagaggagaaattaactATGAGAGGATCGCAT

CACCATCACCATCACATTGAAGGCCGTGCTGCAGCTCCTCCAAGTTACT

G-3'
(EcoRI-site is underlined, coding nucleotides in
capital letters).

Reverse primer (SEQ ID NO. 4):
5'-acgtaagcttTCATTACTTAAAGAACTTAATCTCCGTG-3'
(HindIII-site is underlined, coding nucleotides
in capital letters).
```

The forward primer (besides the EcoRI cloning and ribosomal binding sites) is encoding an N-terminal MRG-SHHHHHHIEGR peptide extension (shown in SEQ ID NO. 2) fused in frame at the 5'-end to the SCRN1 gene. The EcoRI/HindIII digested PCR fragment is ligated into the pQE80L vector (Qiagen, Hilden, Germany). Subsequently, E. coli XL1-blue competent cells are transformed with the generated plasmid. After sequence analysis, E. coli C600 competent cells are transformed with the generated plasmid for IPTG-inducible expression under control of the T5-promoter of the pQE vector series following the manufacturer's instructions.

For purification of the MRGSHHHHHHIEGR-SCRN1 fusion protein, 1 L of an induced over-night bacterial culture is pelleted by centrifugation and the cell pellet is resuspended in lysis buffer (20 mM sodium-phosphate buffer, pH 7.4, 500 mM sodium chloride (NaCl)). Cells are disrupted in a French press with a pressure of 1500 bar. Insoluble material is pelleted by centrifugation (25000 g, 15 min, 4° C.) and the supernatant is applied to Ni-nitrilotriacetic acid (Ni-NTA) metal-affinity column. After application of the antigen, the column is washed with several bed volumes of washing buffer (20 mM sodium-phosphate buffer, pH 7.4, 500 mM NaCl, 20 mM imidazole). Finally, bound antigen is eluted using the washing buffer with a linear gradient of 20 mM-500 mM imidazole, antigene-containing fractions (7 mL each) are identified at O.D.$_{280}$ in an UV-detector. Antigene-containing fractions are pooled, dialyzed against storage buffer (75 mM HEPES, pH 7.5, 100 mM NaCl, 1 mM EDTA, 6.5% (w/v) saccharose) and stored at 4° C. or −80° C., respectively.

Generation of Peptide Immunogens for Immunization

To create polyclonal antibodies that are specific for SCRN1, peptide sequences are identified that show no significant homology to other known human proteins. The amino acid sequence of SCRN1 is run against the data bank of human proteins accessible at the Swiss Institute of Bioinformatics using the software Blast. The amino acid sequence 398-413 shows no significant homology to secernin-2 (SCRN2) or other human proteins and is therefore selected to raise SCRN1 specific antibodies. The respective sequence is synthesized and chemically conjugated to KLH (keyhole limpet hemocyanin) to obtain an immunogen for immunization.

Generation of Polyclonal Antibodies a) Immunization

For immunization, a fresh emulsion of a protein solution (100 µg/ml protein SCRN1 or 500 µg/ml of KLH coupled with a peptide from the SCRN1 amino acids 398-413) and complete Freund's adjuvant at the ratio of 1:1 is prepared. Each rabbit is immunized with 1 ml of the emulsion at days 1, 7, 14 and 30, 60 and 90. Blood is drawn and resulting anti-SCRN1 serum is used for further experiments as described in examples 3 and 4.

b) Purification of IgG (Immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 µl/ml of diluted sample) is added drop-wise under vigorous stirring. After 30 min the sample is centrifuged (13 000×g, 30 min, 4° C.), the pellet discarded and the supernatant collected. The pH of the supernatant is adjusted to 7.5 by the addition of 2 M Tris-base and filtered (0.2 µm).

The immunoglobulin in the supernatant is precipitated under vigorous stirring by the drop-wise addition of a 4 M ammonium sulfate solution to a final concentration of 2 M. The precipitated immunoglobulins are collected by centrifugation (8000×g, 15 min, 4° C.).

The supernatant is discarded. The pellet is dissolved in 10 mM NaH$_2$PO$_4$/NaOH, pH 7.5, 30 mM NaCl and exhaustively dialyzed. The dialysate is centrifuged (13 000×g, 15 min, 4° C.) and filtered (0.2 µm).

Biotinylation of Polyclonal Rabbit IgG

Polyclonal rabbit IgG is brought to 10 mg/ml in 10 mM NaH$_2$PO$_4$/NaOH, pH 7.5, 30 mM NaCl. Per ml IgG solution 50 µl Biotin-N-hydroxysuccinimide (3.6 mg/ml in DMSO) are added. After 30 min at room temperature, the sample is chromatographed on Superdex 200 (10 mM NaH$_2$PO$_4$/NaOH, pH 7.5, 30 mM NaCl). The fraction containing biotinylated IgG are collected. Monoclonal antibodies have been biotinylated according to the same procedure.

Digoxygenylation of Polyclonal Rabbit IgG

Polyclonal rabbit IgG is brought to 10 mg/ml in 10 mM NaH$_2$PO$_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) are added. After 30 min at room temperature, the sample is chromatographed on Superdex 200 (10 mM NaH$_2$PO$_4$/NaOH, pH 7.5, 30 mM NaCl). The fractions containing digoxigenylated IgG are collected. Monoclonal antibodies have been labeled with digoxigenin according to the same procedure.

EXAMPLE 3

Western Blotting for the Detection of SCRN1 in Human Lung Cancer (LC) Tissue Using Polyclonal Antibody as Generated in Example 2

Tissue lysates from tumor samples and healthy control samples are prepared as described in Example 1, "Tissue preparation".

SDS-PAGE and Western-Blotting are carried out using reagents and equipment of Invitrogen, Karlsruhe, Germany. For each tissue sample tested, 15 µg of tissue lysate are diluted in reducing NuPAGE (Invitrogen) SDS sample buffer and heated for 10 min at 95° C. Samples are run on 4-12% NuPAGE gels (Tris-Glycine) in the MES running buffer system. The gel-separated protein mixture is blotted onto nitrocellulose membranes using the Invitrogen XCell II Blot Module (Invitrogen) and the NuPAGE transfer buffer system. The membranes are washed 3 times in PBS/0.05% Tween-20 and blocked with Roti-Block blocking buffer (A151.1; Carl Roth GmbH, Karlsruhe, Germany) for 2 h. The primary antibody, polyclonal rabbit anti-SCRN1 serum (generation described in Example 2), is diluted 1:10,000 in Roti-Block blocking buffer and incubated with the membrane for 1 h. The membranes are washed 6 times in PBS/0.05% Tween-20. The specifically bound primary rabbit antibody is labeled with an POD-conjugated polyclonal sheep anti-rabbit IgG antibody, diluted to 10 mU/ml in 0.5× Roti-Block blocking buffer. After incubation for 1 h, the membranes are washed 6 times in PBS/0.05% Tween-20. For detection of the bound POD-conjugated anti-rabbit antibody, the membrane is incubated with the Lumi-Light$^{PLUS}$ Western Blotting Substrate (Order-No. 2015196, Roche Diagnostics GmbH, Mannheim, Germany) and exposed to an autoradiographic film.

Signal intensity for SCRN1 is increased in 19 out of 20 tumor tissue lysates as obtained from 20 different LC patients (FIG. 1). Thus, the increased abundance of SCRN1 in tumor tissue as detected by MALDI in example 1 is clearly confirmed by Western Blotting analyses.

EXAMPLE 4

ELISA for the Measurement of SCRN1 in Human Serum and Plasma Samples or Other Body Fluids For detection of SCRN1 in human serum or plasma, a sandwich ELISA is developed using the antibodies from example 2. For capture of the antigen the antibody against peptide 398-413 is conjugated with biotin while the antibodies against the SCRN1 full length sequence is conjugated with digoxygenin.

For calibration of the assay LOXIMVI cells, a human melanoma cell line included in the NCI60 tumor cell lines of the US national cancer institute, are propagated and a lysate of the cells is used for calibration. A 1:2500 dilution of the lysat (protein concentration=7.7 mg/ml) was arbitrarily set to 1 U/ml.

Streptavidin-coated 96-well microtiter plates are incubated with 100 µl biotinylated anti-SCRN1, aa 398-413, polyclonal antibody for 60 min at 10 µg/ml in 10 mM phosphate, pH 7.4, 1% BSA, 0.9% NaCl and 0.1% Tween 20. After incubation, plates are washed three times with 0.9% NaCl, 0.1% Tween 20. Wells are then incubated for over night with either a serial dilution of the recombinant protein (see Example 2) as standard antigen or with diluted serum/plasma/ELF samples from patients. After binding of SCRN1, plates are washed three times with 0.9% NaCl, 0.1% Tween 20. For specific detection of bound SCRN1, wells are incubated with 100 µl of digoxygenylated anti-SCRN1 polyclonal antibody for 60 min at 10 µg/ml in 10 mM phosphate, pH 7.4, 1% BSA, 0.9% NaCl and 0.1% Tween 20. Thereafter, plates are washed three times to remove unbound antibody. In a next step, wells are incubated with 50 mU/ml anti-digoxigenin-POD conjugates (Roche Diagnostics GmbH, Mannheim, Germany, Catalog No. 1633716) for 60 min in 10 mM phosphate, pH 7.4, 1% BSA, 0.9% NaCl and 0.1% Tween 20. Plates are subsequently washed three times with the same buffer. For detection of antigen-antibody complexes, wells are incubated with 100 µl ABTS solution (Roche Diagnostics GmbH, Mannheim, Germany, Catalog No. 11685767) and OD is measured after 30-60 min at 405 nm with an ELISA reader.

EXAMPLE 5

SCRN1 as a Serum Marker for Lung Cancer (LC)

Samples derived from 365 well-characterized lung cancer patients (146 adeno-CA, 87 squamous cell CA, 44 small cell CA, 88 other CA of the lung) with the UICC classification given in table 3 are used.

TABLE 3

| Study population | |
| --- | --- |
| Stage according to UICC | Number of samples |
| UICC I/II | 182 |
| UICC III | 118 |
| UICC IV | 62 |
| staging unknown | 3 |
| obviously healthy blood donors | 50 |

Figure 2:
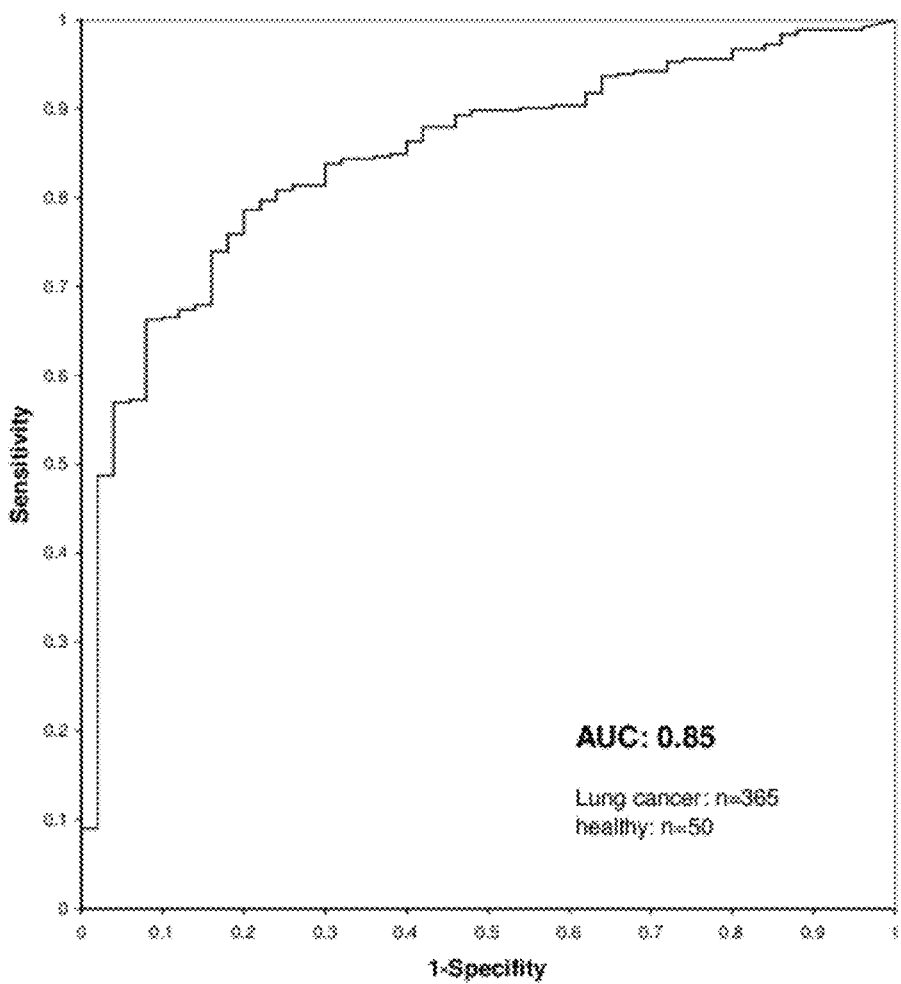
FIG. 2 shows the plot of the receiver operator characteristics (ROC-plot) of SCRN1 in LC samples with an AUC of 0.85 for the assessment of 365 samples obtained from patients with LC as compared to 50 control samples obtained from obviously healthy individuals.

The level of SCRN1 in the LC samples of Table 3 is evaluated in comparison to 50 control samples obtained from obviously healthy individuals (control cohort), with an AUC of 0.85 (FIG. 2).

EXAMPLE 6

SCRN1 as a Serum Marker for Head/Neck Cancer (H/NC)

Samples derived from 30 well-characterized head/neck cancer patients with the UICC classification given in Table 4 are used.

TABLE 4

| Study population | |
| --- | --- |
| Stage according to UICC | Number of samples |
| UICC I/II | 4 |
| UICC III | 3 |
| UICC IV | 21 |
| staging unknown | 2 |
| obviously healthy blood donors | 50 |

Figure 3:
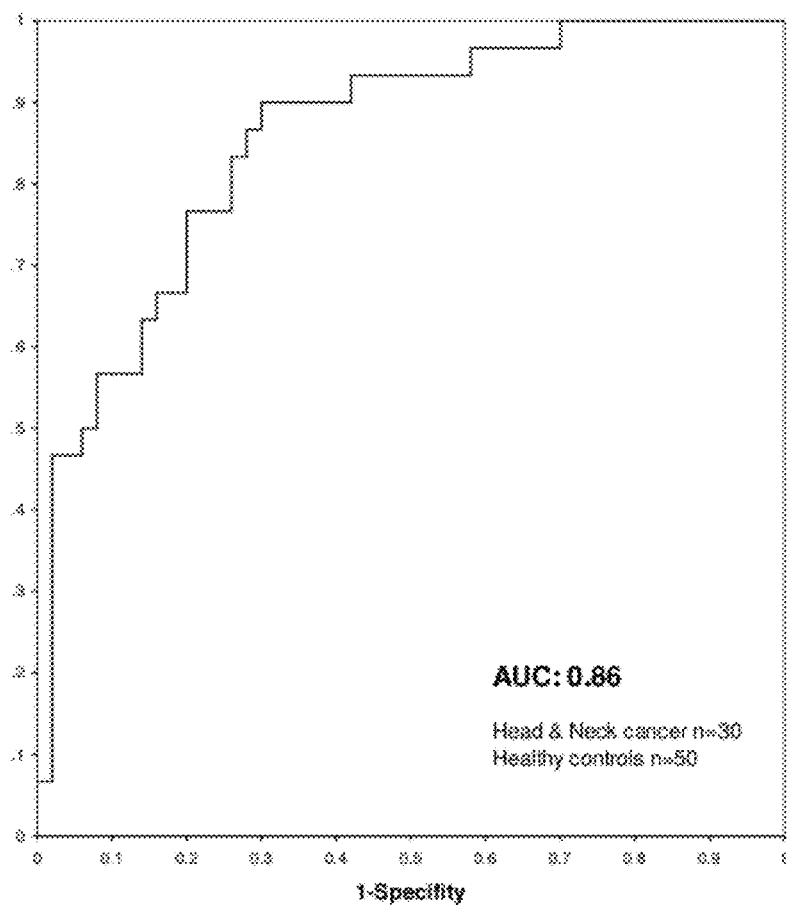
FIG. 3 shows the plot of the receiver operator characteristics (ROC-plot) of SCRN1 in H/NC samples with an AUC of 0.86 for the assessment of 30 samples obtained from patients with head/neck cancer as compared to 50 control samples obtained from obviously healthy individuals.

The level of SCRN1 in the H/NC samples of Table 6 is evaluated in comparison to 50 control samples obtained from obviously healthy individuals (control cohort), resulting in an AUC of 0.86 (FIG. 3)

EXAMPLE 7

SCRN1 as a Serum Marker for Endometrium Cancer (EC)

Samples derived from 23 well-characterized endometrium cancer patients with the UICC classification given in Table 5 are used.

TABLE 5

| Study population | |
| --- | --- |
| Stage according to UICC | Number of samples |
| UICC I/II | 12 |
| UICC III | 3 |
| UICC IV | 3 |
| staging unknown | 5 |
| obviously healthy blood donors | 50 |

Figure 4:
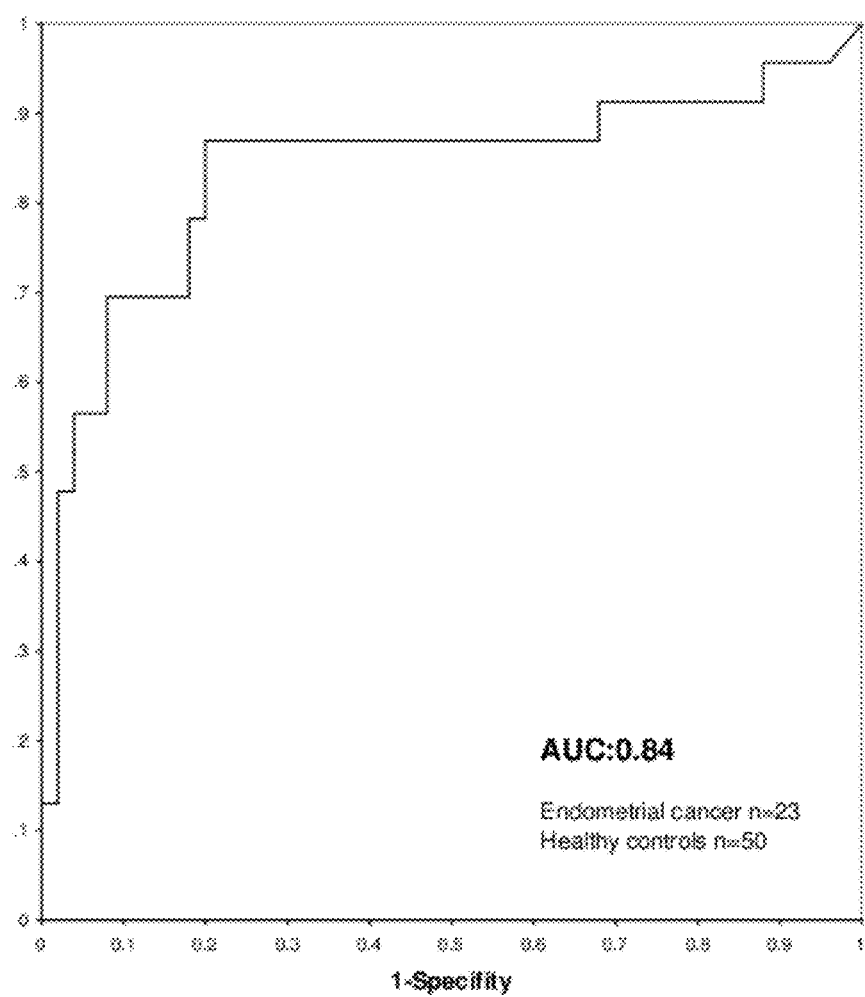
FIG. 4 shows the plot of the receiver operator characteristics (ROC-plot) of SCRN1 in EC samples with an AUC of 0.84 for the assessment of 23 samples obtained from patients with endometrium cancer as compared to 50 control samples obtained from obviously healthy individuals.

The level of SCRN1 in the EC samples of Table 6 is evaluated in comparison to 50 control samples obtained from obviously healthy individuals (control cohort), resulting in an AUC of 0.84 (FIG. 4)

EXAMPLE 8

SCRN1 as a Serum Marker for Ovarian Cancer (OC)

Samples derived from 42 well-characterized ovarian cancer (OC) patients with the UICC classification given in Table 6 are used.

TABLE 6

| Study population | |
|---|---|
| Stage according to UICC | Number of samples |
| UICC I/II | 7 |
| UICC III | 14 |
| UICC IV | 9 |
| staging unknown | 12 |
| obviously healthy blood donors | 50 |

Figure 5:
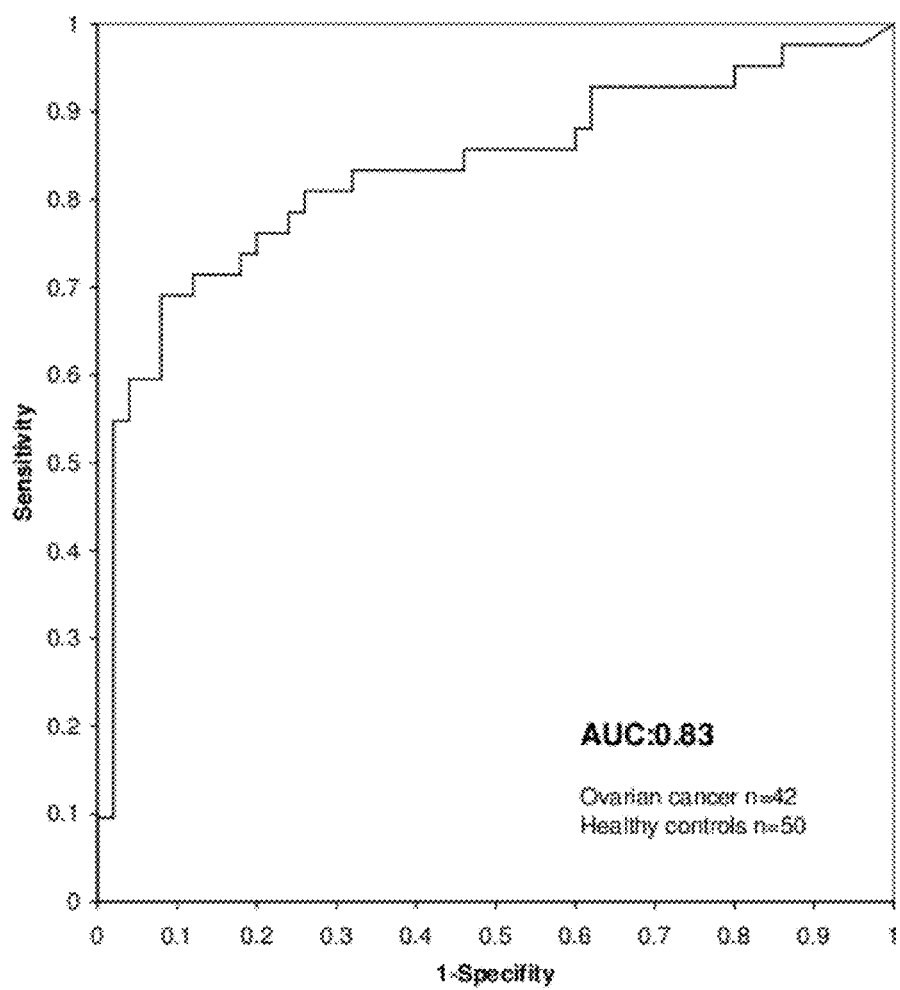
FIG. 5 shows the plot of the receiver operator characteristics (ROC-plot) of SCRN1 in OC samples with an AUC of 0.83 for the assessment of 42 samples obtained from patients with ovarian cancer as compared to 50 control samples obtained from obviously healthy individuals.

The level of SCRN1 in the OC samples of Table 6 is evaluated in comparison to 50 control samples obtained from obviously healthy individuals (control cohort), resulting in an AUC of 0.83 (FIG. 5)

EXAMPLE 9

SCRN1 as a Serum Marker for Malignant Melanoma (MM)

Samples derived from 16 well-characterized malignant melanoma patients with the UICC classification given in Table 7 are used.

TABLE 7

| Study population | |
|---|---|
| Stage according to UICC | Number of samples |
| UICC I/II | 3 |
| UICC III | 1 |
| UICC IV | 0 |
| staging unknown | 12 |
| obviously healthy blood donors | 50 |

Figure 6:
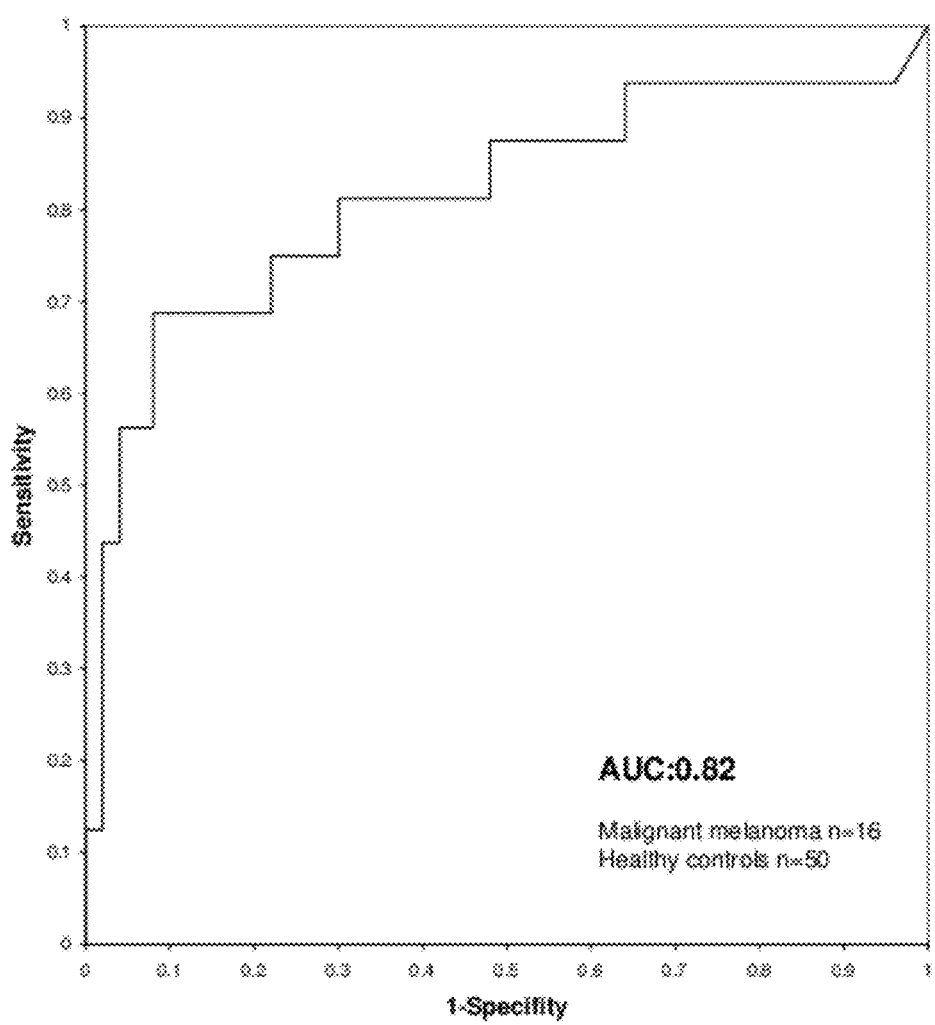
FIG. 6 shows the plot of the receiver operator characteristics (ROC-plot) of SCRN1 in MM samples with an AUC of 0.82 for the assessment of 16 samples obtained from patients with malignant melanoma as compared to 50 control samples obtained from obviously healthy individuals.
Figure 7:
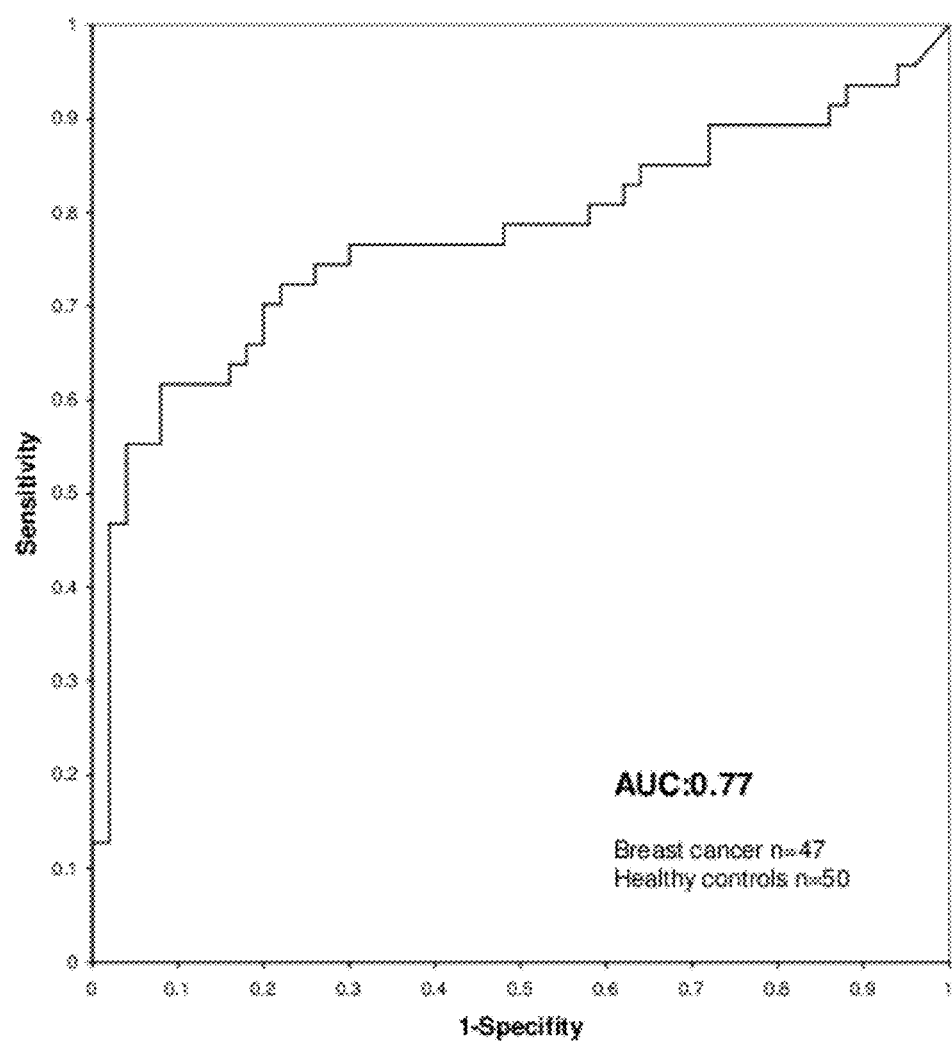
FIG. 7 shows the plot of the receiver operator characteristics (ROC-plot) of SCRN1 in BC samples with an AUC of 0.77 for the assessment of 47 samples obtained from patients with breast cancer as compared to 50 control samples obtained from obviously healthy individuals.

The level of SCRN1 in the MM samples of Table 6 is evaluated in comparison to 50 control samples obtained from obviously healthy individuals (control cohort), resulting in an AUC of 0.82 (FIG. 6)

EXAMPLE 10

SCRN1 as a Serum Marker for Breast Cancer (BC)

Samples derived from 47 well-characterized breast cancer patients with the UICC classification given in Table 8 are used.

TABLE 8

| Study population | |
|---|---|
| Stage according to UICC | Number of samples |
| UICC I/II | 26 |
| UICC III | 9 |
| UICC IV | 12 |
| obviously healthy blood donors | 50 |

The level of SCRN1 in the BC samples of Table 5 is evaluated in comparison to 50 control samples obtained from obviously healthy individuals (control cohort), resulting in an AUC of 0.77 (FIG. 6).

EXAMPLE 11

SCRN1 as a Serum Marker for Cervix Cancer (CC)

Samples derived from 20 well-characterized cervix cancer patients with the UICC classification given in Table 9 are used.

TABLE 9

| Study population | |
|---|---|
| Stage according to UICC | Number of samples |
| UICC is/I/II | 11 |
| UICC III | 7 |
| UICC IV | 2 |
| staging unknown | 0 |
| obviously healthy blood donors | 50 |

Figure 8:
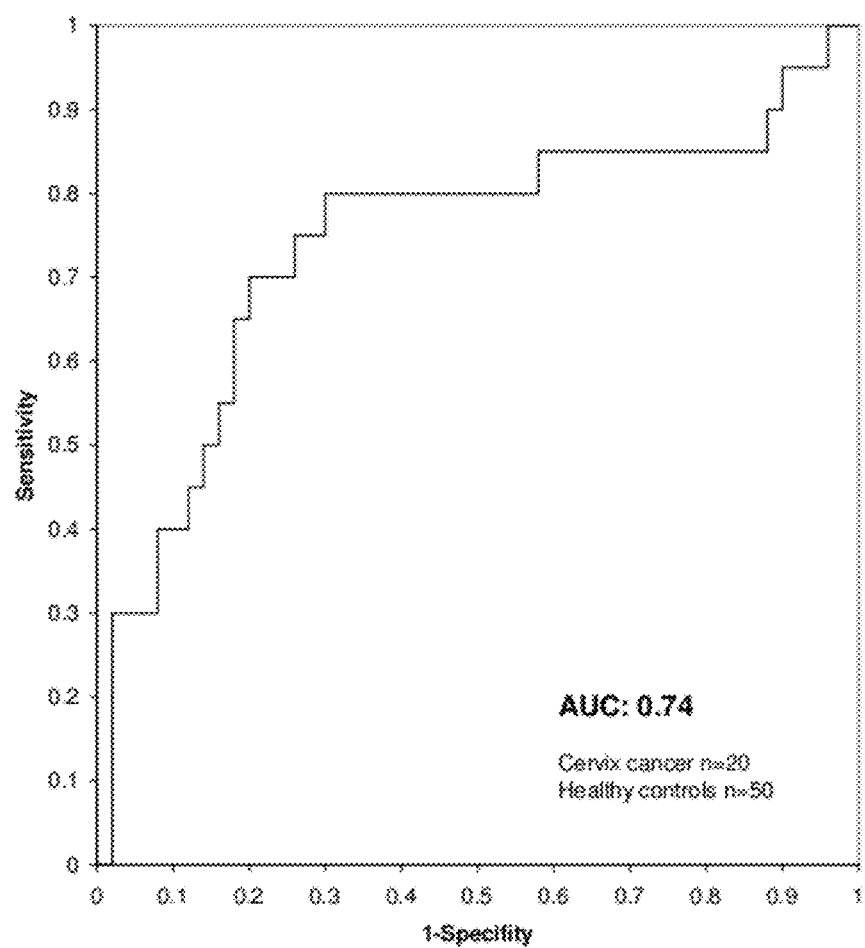
FIG. 8 shows the plot of the receiver operator characteristics (ROC-plot) of SCRN1 in CC samples with an AUC of 0.74 for the assessment of 20 samples obtained from patients with cervix cancer as compared to 50 control samples obtained from obviously healthy individuals.

The level of SCRN1 in the CC samples of Table 6 is evaluated in comparison to 50 control samples obtained from obviously healthy individuals (control cohort), resulting in an AUC of 0.74 (FIG. 8)

EXAMPLE 12

SCRN1 as a Serum Marker for Pancreas Cancer (PAC)

Samples derived from 49 well-characterized pancreas cancer patients with the UICC classification given in Table 10 are used.

TABLE 10

| Study population | |
|---|---|
| Stage according to UICC | Number of samples |
| UICC I/II | 26 |
| UICC III | 5 |
| UICC IV | 15 |
| Staging unknown | 3 |
| obviously healthy blood donors | 50 |

Figure 9:
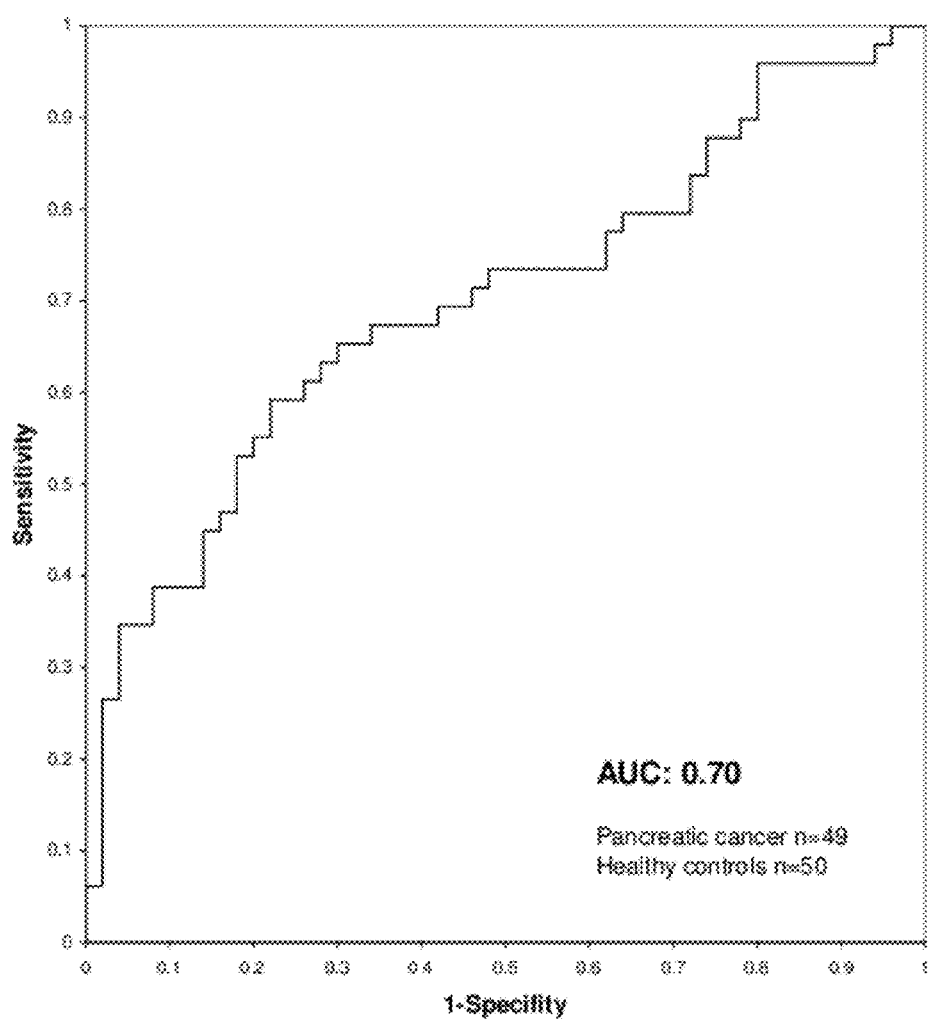
FIG. 9 shows the plot of the receiver operator characteristics (ROC-plot) of SCRN1 in PAC samples with an AUC of 0.70 for the assessment of 49 samples obtained from patients with pancreas cancer as compared to 50 control samples obtained from obviously healthy individuals.

The level of SCRN1 in the PAC samples of Table 6 is evaluated in comparison to 50 control samples obtained from obviously healthy individuals (control cohort), resulting in an AUC of 0.70 (FIG. 9)

EXAMPLE 13

SCRN1 as a Serum Marker for Colorectal Cancer (CRC)

Samples derived from 50 well-characterized colorectal cancer patients with the UICC classification given in Table 11 are used.

TABLE 11

| Study population | |
|---|---|
| Stage according to UICC | Number of samples |
| UICC I/II | 25 |
| UICC III | 13 |
| UICC IV | 6 |
| staging unknown | 6 |
| obviously healthy blood donors | 50 |

Figure 10:
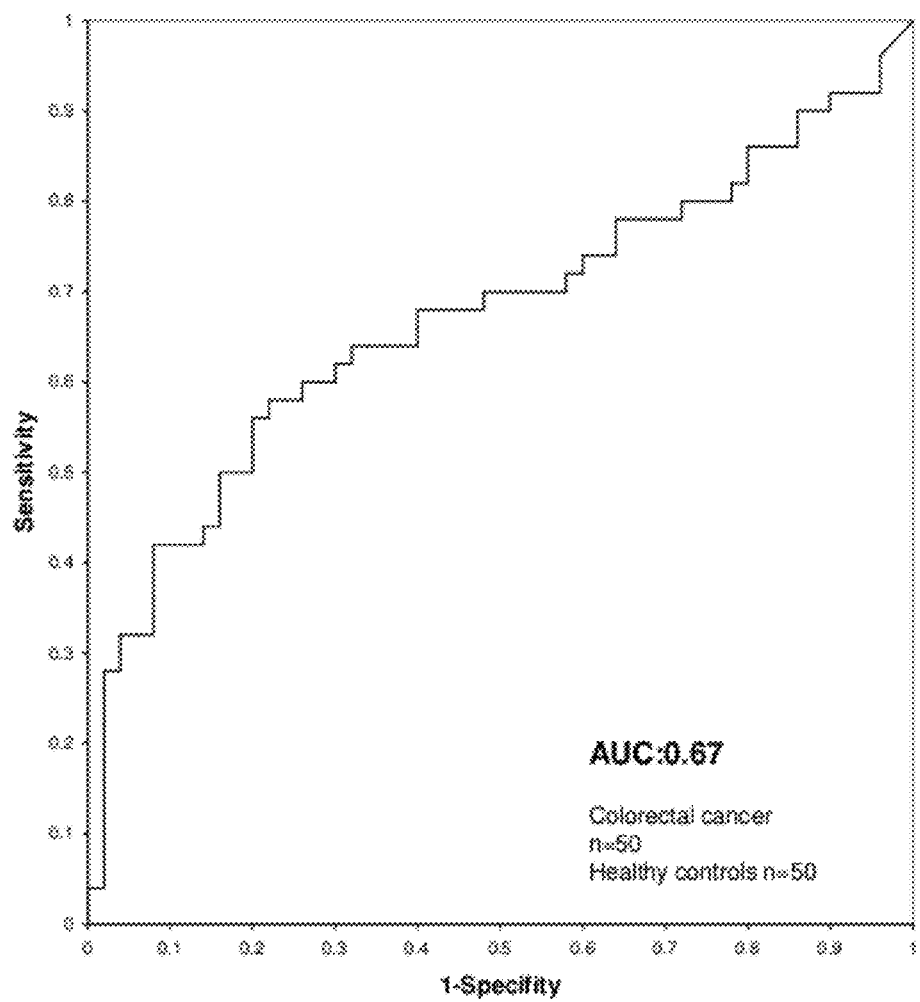
FIG. 10 shows the plot of the receiver operator characteristics (ROC-plot) of SCRN1 in CRC samples with an AUC of 0.67 for the assessment of 50 samples obtained from patients with colorectal cancer as compared to 50 control samples obtained from obviously healthy individuals.

The level of SCRN1 in the CRC samples of Table 4 is evaluated in comparison to 50 control samples obtained from obviously healthy individuals (control cohort), resulting in an AUC of 0.67 (FIG. 10)

EXAMPLE 14

SCRN1 as a Serum Marker for Bladder Cancer (BLC)

Samples derived from 50 well-characterized bladder cancer patients with the UICC classification given in Table 12 are used.

TABLE 12

| Study population | |
| --- | --- |
| Stage according to UICC | Number of samples |
| UICC 0/I/II | 42 |
| UICC III | 1 |
| UICC IV | 3 |
| staging unknown | 4 |
| obviously healthy blood donors | 50 |

Figure 11:
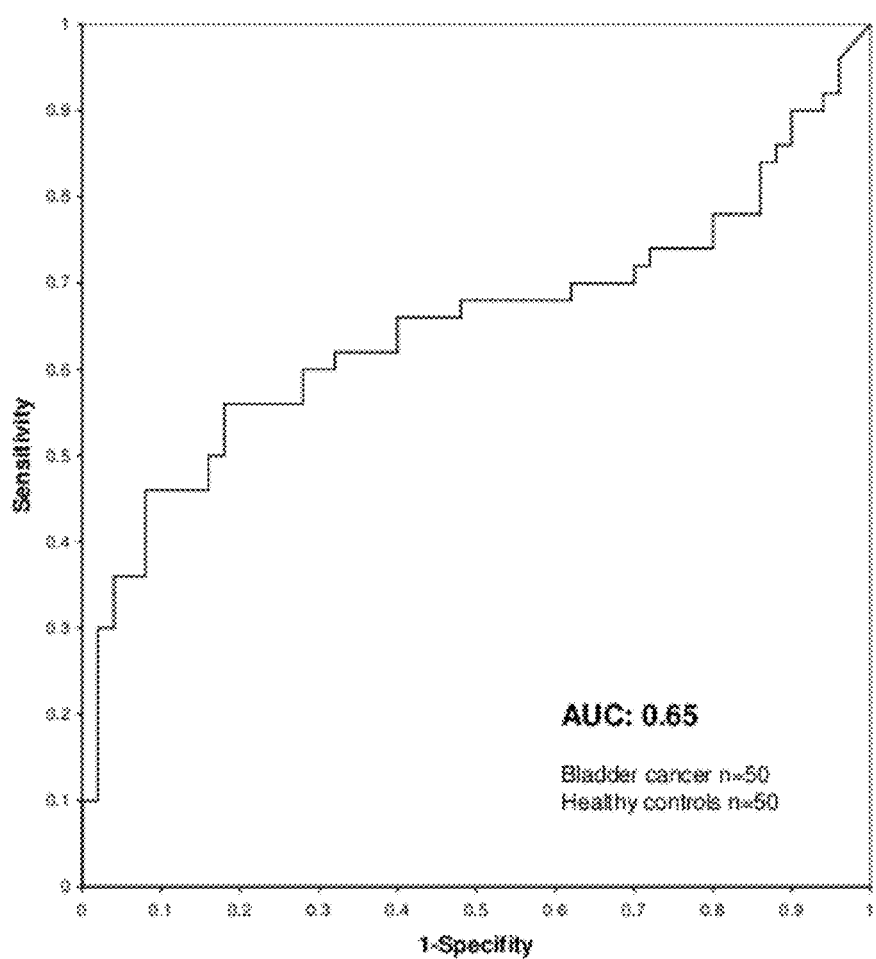
FIG. 11 shows the plot of the receiver operator characteristics (ROC-plot) of SCRN1 in BLC samples with an AUC of 0.65 for the assessment of 50 samples obtained from patients with ovarian cancer as compared to 50 control samples obtained from obviously healthy individuals.

The level of SCRN1 in the PC samples of Table 6 is evaluated in comparison to 50 control samples obtained from obviously healthy individuals (control cohort), resulting in an AUC of 0.65 (FIG. 11)

EXAMPLE 15

SCRN1 as a Serum Marker for Kidney Cancer (KC)

Samples derived from 25 well-characterized endometrium cancer patients with the UICC classification given in Table 13 are used.

TABLE 13

| Study population KG | |
| --- | --- |
| Stage according to UICC | Number of samples |
| UICC I/II | 13 |
| UICC III | 4 |
| UICC IV | 3 |
| staging unknown | 5 |
| obviously healthy blood donors | 50 |

Figure 12:
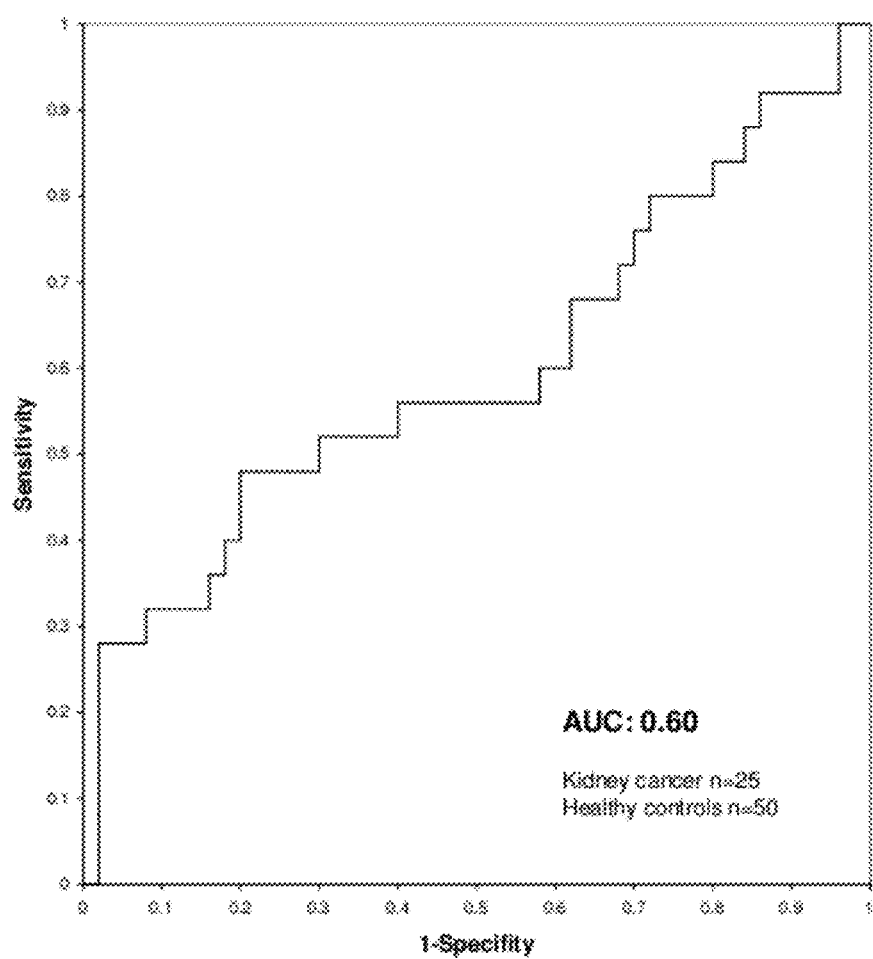
FIG. 12 shows the plot of the receiver operator characteristics (ROC-plot) of SCRN1 in KC samples with an AUC of 0.60 for the assessment of 25 samples obtained from patients with kidney cancer as compared to 50 control samples obtained from obviously healthy individuals.

The level of SCRN1 in the KC samples of Table 6 is evaluated in comparison to 50 control samples obtained from obviously healthy individuals (control cohort), resulting in an AUC of 0.60 (FIG. 12)

EXAMPLE 16

SCRN1 as a Serum Marker for Prostate Cancer (PC)

Samples derived from 50 well-characterized prostate cancer patients with the UICC classification given in Table 14 are used.

TABLE 14

| Study population PC | |
| --- | --- |
| Stage according to UICC | Number of samples |
| UICC I/II | 24 |
| UICC III | 4 |
| UICC IV | 6 |
| staging unknown | 16 |
| obviously healthy blood donors | 50 |

Figure 13:
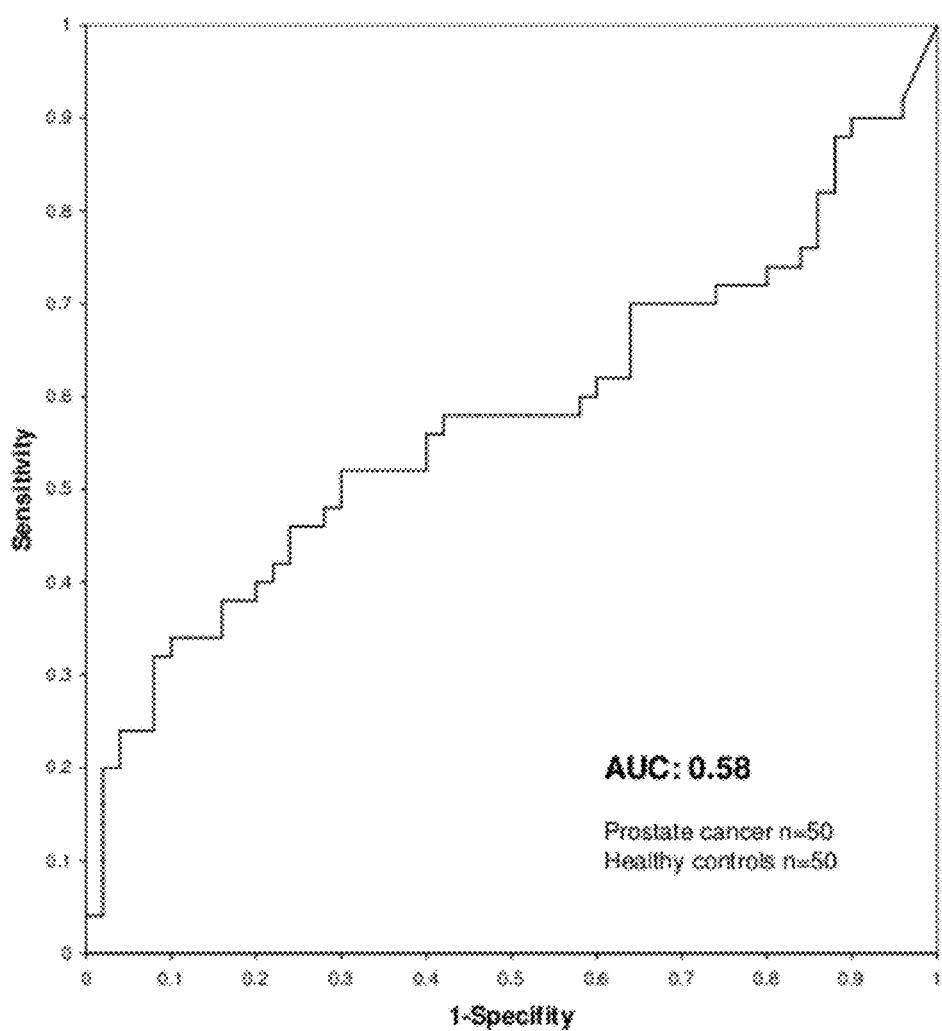
FIG. 13 shows the plot of the receiver operator characteristics (ROC-plot) of SCRN1 in PC samples with an AUC of 0.58 for the assessment of 50 samples obtained from patients with prostate cancer as compared to 50 control samples obtained from obviously healthy individuals.

The level of SCRN1 in the PC samples of Table 6 is evaluated in comparison to 50 control samples obtained from obviously healthy individuals (control cohort), resulting in an AUC of 0.58 (FIG. 13)

EXAMPLE 17

SCRN1 in Epithelial Lining Fluid (ELF)—Bronchoscopic Microsampling

Bronchoscopic microsampling (BMS) offers the possibility to collect epithelial lining fluid (ELF) near small pulmonary nodules in a largely non-invasive manner. Subsequently, it is possible to measure concentrations of tumor markers in ELF in order to identify a malignant nodule. A patient specific baseline concentration of the respective tumor marker is obtained by sampling ELF in the contralateral lung.

The BMS probe (Olympus Medical Systems Corp. Tokyo, Japan, Cat.-No.: BC-402C) is inserted into the lungs through the bronchoscope and consists of an outer polyethylene sheath and an inner cotton probe attached to a stainless steel guide. The inner probe is advanced to the proximity of the nodule and BMS is performed for a few seconds. Afterwards, the inner probe is withdrawn into the outer sheath and both devices are withdrawn simultaneously. The cotton tip is cut off and directly frozen at −80° C. For the determination, ELF is eluted from the cotton tip and can be analyzed subsequently. The concentration of SCRN1 is determined in ELF with the ELISA as described in Example 4.

SCRN1 was detectable in ELF from patients with a pulmonary mass detected by computer tomography. Abbreviations used in table 15 are PM (lung with pulmonary mass) and Cl (contralateral lung). Where a final, cancer related diagnosis was available it is given in the table.

TABLE 15

| Detection of SCRN1 in ELF | | |
| --- | --- | --- |
| Patient | Diagnosis | SCRN1 [U/ml] |
| ELF_1_PM | Small cell lung carcinoma | 5.89 |
| ELF_1_Cl | | 0.00 |
| ELF_2_PM | Final diagnosis unknown | 3.87 |
| ELF_2_Cl | | 0.83 |
| ELF_3_PM | Relapsing squamous carcinoma | 0.13 |
| ELF_3_Cl | | 2.78 |
| ELF_4_PM | Adenocarcinoma | 4.08 |
| ELF_4_Cl | | 2.65 |
| ELF_5_PM | Final diagnosis unknown | 2.59 |
| ELF_5_Cl | | 1.78 |
| ELF_6_PM | Benign pulmonary mass | 2.14 |
| ELF_6_Cl | | 2.01 |
| ELF_7_PM | Final diagnosis unknown | 0.21 |
| ELF_7_Cl | | 0.00 |
| ELF_8_PM | Final diagnosis unknown | 3.35 |
| ELF_8_Cl | | 0.73 |
| ELF_9_PM | Final diagnosis unknown | 1.87 |
| ELF_9_Cl | | 0.06 |
| ELF_10_PM | Final diagnosis unknown | 1.50 |
| ELF_10_Cl | | 0.00 |

What is claimed is:

1. A method for in vitro assessment of a presence of cancer selected from the group consisting of lung, ovary, endometrial, melanoma, breast, head and neck, bladder, pancreas, cervix, kidney, and prostate cancer in a patient suspected of having cancer selected from the group consisting of lung, ovary, endometrial, melanoma, breast, head and neck, bladder, pancreas, cervix, kidney and prostate cancer, the method comprising
   a) detecting a full-length secernin-1 protein (SCRN1) in a body fluid sample from the patient by contacting, in vitro, the body fluid sample with an antibody that specifically binds to an epitope located in amino acids 398-413 of SEQ ID NO:1, wherein the antibody and the full-length SCRN1 form a complex;
   b) quantifying a signal from the complex to obtain a concentration of the full-length SCRN1 in the complex;
   c) analyzing the concentration of the full-length SCRN1 obtained in said step of quantifying to a SCRN1 reference concentration obtained from a normal control; and
   d) providing a diagnosis of the presence of cancer selected from the group consisting of lung, ovary, endometrium, melanoma, breast, head and neck, bladder, pancreas, cervix, kidney, and prostate cancer if the concentration of the full-length SCRN1 obtained in said step of quantifying is greater than the SCRN1 reference concentration obtained from the normal control.

2. The method according to claim 1, further comprising:
   detecting in a body fluid sample from the patient a marker selected from the group consisting of carcinoembryonic antigen (CEA), neuron-specific enolase (NSE), carbohydrate antigen 19-9 (CA 19-9), carbohydrate antigen 125 (CA 125), prostate specific antigen (PSA), pro-gastrin releasing peptide (proGRP), squamous cell carcinoma antigen (SCC), nicotinamide N-methyltransferase (NNMT), anti-p53 autoantibodies, seprase, and soluble dipeptidyl peptidase IV/seprase complex (DPPIV/seprase complex) by contacting, in vitro, the body fluid sample with a second antibody that specifically binds to the marker, wherein the second antibody and the marker form a complex;
   b) quantifying a signal from the complex to obtain a concentration of the marker in the complex;

c) analyzing the concentration of the marker obtained in said step of quantifying to a marker reference concentration obtained from a normal control; and d) providing a diagnosis of presence of cancer if the concentration of the marker obtained in said step of quantifying is greater than the marker reference concentration obtained from the normal control.

3. A kit for performing the method according to claim 1 comprising reagents for detecting a concentration of SCRN1, wherein at least one reagent is an antibody that specifically binds to an epitope located in amino acids 398-413 of SEQ ID NO:1.

4. A kit for performing the method according to claim 2 comprising reagents for detecting a concentration of SCRN1, wherein at least one reagent is an antibody that specifically binds to an epitope located in amino acids 398-413 of SEQ ID NO:1 and reagents for detecting a concentration of the marker.

* * * * *

SEQUENCE LISTING

<160> NUMBER OF SEQ ID NOS: 4

<210> SEQ ID NO 1
<211> LENGTH: 414
<212> TYPE: PRT
<213> ORGANISM: Homo sapiens

<400> SEQUENCE: 1

Met Ala Ala Pro Pro Ser Tyr Cys Phe Val Ala Phe Pro Pro Arg
1               5                   10                  15

Ala Lys Asp Gly Leu Val Val Phe Gly Lys Asn Ser Ala Arg Pro Arg
            20                  25                  30

Asp Glu Val Gln Glu Val Val Tyr Phe Ser Ala Ala Asp His Glu Pro
        35                  40                  45

Glu Ser Lys Val Glu Cys Thr Tyr Ile Ser Ile Asp Gln Val Pro Arg
    50                  55                      60

Thr Tyr Ala Ile Met Ile Ser Arg Pro Ala Trp Leu Trp Gly Ala Glu
65                  70                  75                  80

Met Gly Ala Asn Glu His Gly Val Cys Ile Ala Asn Glu Ala Ile Asn
                85                  90                  95

Thr Arg Glu Pro Ala Ala Glu Ile Glu Ala Leu Leu Gly Met Asp Leu
            100                 105                 110

Val Arg Leu Gly Leu Glu Arg Gly Glu Thr Ala Lys Glu Ala Leu Asp
            115                 120                 125

Val Ile Val Ser Leu Leu Glu Glu His Gly Gln Gly Gly Asn Tyr Phe
            130                 135                 140

Glu Asp Ala Asn Ser Cys His Ser Phe Gln Ser Ala Tyr Leu Ile Val
145                 150                 155                 160

Asp Arg Asp Glu Ala Trp Val Leu Glu Thr Ile Gly Lys Tyr Trp Ala
                165                 170                 175

Ala Glu Lys Val Thr Glu Gly Val Arg Cys Ile Cys Ser Gln Leu Ser
            180                 185                 190

Leu Thr Thr Lys Met Asp Ala Glu His Pro Glu Leu Arg Ser Tyr Ala
            195                 200                 205

Gln Ser Gln Gly Trp Trp Thr Gly Glu Gly Glu Phe Asn Phe Ser Glu
        210                 215                 220

Val Phe Ser Pro Val Glu Asp His Leu Asp Cys Gly Ala Gly Lys Asp
225                 230                 235                 240

Ser Leu Glu Lys Gln Glu Glu Ser Ile Thr Val Gln Thr Met Met Asn
                245                 250                 255

Thr Leu Arg Asp Lys Ala Ser Gly Val Cys Ile Asp Ser Glu Phe Phe
            260                 265                 270

Leu Thr Thr Ala Ser Gly Val Ser Val Leu Pro Gln Asn Arg Ser Ser
            275                 280                 285

Pro Cys Ile His Tyr Phe Thr Gly Thr Pro Asp Pro Ser Arg Ser Ile
        290                 295                 300

Phe Lys Pro Phe Ile Phe Val Asp Asp Val Lys Leu Val Pro Lys Thr
305                 310                 315                 320

Gln Ser Pro Cys Phe Gly Asp Asp Pro Ala Lys Lys Glu Pro Arg
                325                 330                 335

Phe Gln Glu Lys Pro Asp Arg Arg His Glu Leu Tyr Lys Ala His Glu
            340                 345                 350

Trp Ala Arg Ala Ile Ile Glu Ser Asp Gln Gly Gln Gly Arg Lys Leu
            355                 360                 365

```
Arg Ser Thr Met Leu Glu Leu Glu Lys Gln Gly Leu Glu Ala Met Glu
    370                 375                 380

Glu Ile Leu Thr Ser Ser Glu Pro Leu Asp Pro Ala Glu Val Gly Asp
385                 390                 395                 400

Leu Phe Tyr Asp Cys Val Asp Thr Glu Ile Lys Phe Phe Lys
                405                 410

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide extension

<400> SEQUENCE: 2

Met Arg Gly Ser His His His His His His Ile Glu Gly Arg
1               5                   10

<210> SEQ ID NO 3
<211> LENGTH: 96
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 3
acgtgaattc attaaagagg agaaattaac tatgagagga tcgcatcacc atcaccatca      60
cattgaaggc cgtgctgcag ctcctccaag ttactg                                96

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 4
acgtaagctt tcattactta aagaacttaa tctccgtg                              38
```